(12) United States Patent
Labaer et al.

(10) Patent No.: US 6,800,453 B2
(45) Date of Patent: Oct. 5, 2004

(54) NUCLEIC-ACID PROGRAMMABLE PROTEIN ARRAYS

(75) Inventors: Joshua Labaer, Jamaica Plain, MA (US); Albert Lau, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/055,432

(22) Filed: Jan. 22, 2002

(65) Prior Publication Data

US 2002/0192673 A1 Dec. 19, 2002

Related U.S. Application Data

(60) Provisional application No. 60/263,607, filed on Jan. 23, 2001.

(51) Int. Cl.[7] .......................... C12P 21/06; C12M 1/00; C12M 1/34; C12M 3/00

(52) U.S. Cl. ................ 435/68.1; 435/283.1; 435/287.1; 435/287.9; 435/288.3; 435/288.4

(58) Field of Search ............................. 435/68.1, 283.1, 435/287.1, 287.9, 288.3, 288.4, 6, 91.2, 320.1; 530/350, 23.4

(56) References Cited

U.S. PATENT DOCUMENTS

| | | | |
|---|---|---|---|
| 5,445,934 A | 8/1995 | Fodor et al. | |
| 5,641,641 A | 6/1997 | Wood | |
| 5,874,564 A | 2/1999 | Ecker et al. | |
| 5,888,732 A | 3/1999 | Hartley et al. | |
| 5,922,617 A | * 7/1999 | Wang | 436/518 |
| 6,143,557 A | 11/2000 | Hartley et al. | |
| 6,406,921 B1 | * 6/2002 | Wagner | 436/518 |
| 6,420,150 B1 | * 7/2002 | Guegler | 435/193 |
| 6,511,803 B1 | 1/2003 | Church et al. | |

FOREIGN PATENT DOCUMENTS

| | | | |
|---|---|---|---|
| EP | 0 818 467 B1 | 11/2000 | |
| WO | WO 90/05785 | * 5/1990 | ............ 436/518 |
| WO | WO 98/31700 | 7/1998 | |
| WO | WO 99/06833 | 2/1999 | |
| WO | WO 99/11777 | 3/1999 | |
| WO | WO 99/51773 | 10/1999 | |
| WO | WO 00/04382 | 1/2000 | |
| WO | WO 01/40803 A1 | 6/2001 | |
| WO | WO 01/51663 | 7/2001 | |
| WO | WO 01/57198 A2 | 8/2001 | |
| WO | WO 01/68671 A1 | 9/2001 | |
| WO | WO 01/98458 A2 | 12/2001 | |
| WO | WO 01/98534 A2 | 12/2001 | |
| WO | WO 02/14860 | 2/2002 | |
| WO | WO 02/18648 | 3/2002 | |

OTHER PUBLICATIONS deWildt et al., "Antibody arrays for high–throughput screening of antibody–antigen interactions", *Nature Biotechnology* 18:989–994 (2000).

Garcia–Parajo et al., "Real–time light–driven dynamics of the fluorescence emission in single green fluorescent protein molecules", *Proc. Natl. Acad. Sci.* 97:7237–7242 (2000).

Ge, "UPA, a univeral protein array system for quantitative detection of protein–protein, protein–DNA, protein–RNA and protein–ligand interactions", *Nucleic Acids Res.* 28, e3, i–vii (2000).

He and Taussig, "Single step generation of protein arrays from DNA by cell–free expression and in situ immobilisation (PISA method)", *Nucleic Acids Res.* 29, e73, 1–6 (2001).

(List continued on next page.)

*Primary Examiner*—Jeffrey Fredman
*Assistant Examiner*—Teresa E Strzelecka
(74) *Attorney, Agent, or Firm*—Fish & Richardson P.C.

(57) ABSTRACT

Arrays of polypeptides are generated by translation of nucleic acid sequences encoding the polypeptides at a plurality of addresses on the array.

64 Claims, 6 Drawing Sheets

OTHER PUBLICATIONS

Institute of Proteomics Research Web page, *www.hip.harvard.edu/research.html*, printed Oct. 25, 2000.

Lueking et al., "Protein microarrays for gene expression and antibody screening", *Anal. Biochem.* 270:103–111 (1999).

MacBeath and Schreiber, "Printing proteins as microarrays for high–throughput function determination", *Science* 289:1760–1763 (2000).

Martzen et al., "A biochemical genomics approach for identifying genes by the activity of their products", *Science* 286:1153–1155 (1999).

Mendoza et al., "High–throughput microarray–based enzyme–linked immunosorbent assay (ELISA)", *BioTechniques* 27:778–788 (1999).

Rachez et al., "A novel protein complex that interacts with the vitamin D3 receptor in a ligand–dependent manner and enhances VDR transactivation in a cell–free system", *Genes Dev.* 12:1787–1800 (1998).

Rachez et al., "Ligand–dependent transcription activation by nuclear receptors requires the DRIP complex", *Nature* 398:824–828 (1999).

Rachez and Freedman, "Mechanisms of gene regulation by vitamin D3 receptor: a network of coactivator interactions", *Gene* 246:9–21 (2000).

Ross–Macdonald et al., "Large–scale analysis of the yeast genome by transposon tagging and gene disruption ", *Nature* 402:413–418 (1999).

Uetz et al., "A comprehensive analysis of protein–protein interactions in *Saccharomyces cerevisiae*", *Nature* 403:623–631 (2000).

Walhout et al., "Protein interaction mapping in *C. elegans* using proteins involved in vulval development", *Science* 287:116–122 (2000).

Zhu et al., "Analysis of yeast protein kinases using protein chips", *Nature Genetics*, 26:283–289 (2000).

Braun et al., "Proteome–scale purification of human proteins from bacteria", *PNAS* 99(5):2654–2659 (2002).

Brizuela et al., "FLEXGene repository: from sequenced genomes to gene repositories for high–throughput functional biology and proteomics", *Mol. Biochem. Parasitol.* 118:155–165 (2001).

Brizuela et al., "The FLEXGene repository: exploiting the fruits of the genome projects by creating a needed resource to face the challenges of the post–genomic era", *Arch Med Res.* 33:318–324 (2002).

He et al., "DiscernArray technology: a cell–free method for the generation of protein arrays from PCR DNA", *J. Immunol. Methods* 274:265–270 (2003).

LaBaer, "Genomics, proteomics, and the new paradigm in biomedical research", *Genet Med.* 4(6):2S–9S (2002).

Ohuchi et al., "*In vitro* method for the generation of protein libraries using PCR amplification of a single DNA molecule and coupled transcription/translation", *Nucleic Acids Res.* 26(19):4339–4346 (1998).

* cited by examiner

NUCLEIC-ACID PROGRAMMABLE PROTEIN ARRAYS

CROSS-REFERENCE TO RELATED APPLICATIONS

This application claims benefit to its Provisional Application No. 60/263,607 filed Jan. 23, 2001.

BACKGROUND OF THE INVENTION

The swift pace of discovery of new gene products by genomics and proteomics efforts and the growing availability of vast repositories of genes necessitates a strategy for analyzing proteins in a high-throughput manner. The high-density array format lends itself well to ordered high-throughput experimentation and analysis and has therefore become an established and widely-used format for high-throughput analysis of nucleic acids. Nucleic acid microarrays have enabled researchers to compare the expression of thousands of genes simultaneously. By making such comparisons, the expression patterns of clusters of genes in a particular biological context can be rapidly identified, which in turn can indicate groups of proteins that may act in concert in a specific pathway or process.

Reports of the analysis of protein function on a large scale are only just emerging. For example, a large-scale analysis of gene function in S. cerevisiae has been performed using a transposon-tagging strategy for the genome-wide characterization of disruption phenotypes, gene expression, and protein localization (Ross-Macdonald et al., Nature 402:413–418, 1999). In addition, complete two-hybrid analysis has been done using a large matrix of proteins for the interaction mapping of C. elegans proteins involved in vulval development (Walhout et al (2000) Science 287:116–122) and the S. cerevisiae genome (Uetz et al. (2000) Nature 403, 623–631); and Schwikowski (2000) Nature Biotech. 18:1257).

The concept of nonliving peptide and protein arrays has drawn considerable attention because this approach to high-throughput experimentation allows the direct analysis of discrete protein binding and enzymatic activities without the complications of adverse in vivo effects. For example, a low-density (96 well format) protein array has been developed in which proteins, spotted onto a nitrocellulose membrane and biomolecular interactions, were visualized by autoradiography Ge, H. ((2000) Nucleic Acids Res. 28:e3, I–VII). In another example, a high-density protein array (100,000 samples within 222×222 mm) that was used for antibody screening was formed by spotting proteins onto polyvinylidene difluoride (PVDF) (Lueking et al. (1999) Anal. Biochem. 270:103–111). Proteins have been printed on a flat glass plate that contained wells formed by an enclosing hydrophobic Teflon mask, and the arrayed antigens were detected using enzyme-linked immunosorbent assay (ELISA) techniques (Mendoza et al. (1999) Biotechniques 27:778–788.). A large-scale in vitro analysis of biochemical activity using affinity-purified yeast proteins has been performed in the context of an array of 6144 yeast strains, each bearing a plasmid expressing a different GST-ORF fusion (Martzen et al. (1999) Science 286, 1153–1155). Proteins have been covalently linked to chemically derivatized flat glass slides in a high-density array (1600 spots per square centimeter), and protein-protein and protein-small molecule interactions were detected by fluorescence or radioactive decay (MacBeath and Schreiber (2000) Science 289:1760–1763). De Wildt et al. generated a high-density array of 18,342 bacterial clones, each expressing a different single-chain antibody, for screening antibody-antigen interactions (De Wildt et al. (2000) Nature Biotech. 18:989–994).

SUMMARY OF THE INVENTION

The inventors have discovered, among other things, that arrays of polypeptides can be generated by translation of nucleic acid sequences encoding the polypeptides at individual addresses on the array. This allows for the rapid and versatile development of a polypeptide microarray platform for analyzing and manipulating biological information.

In one aspect, the invention features an array including a substrate having a plurality of addresses. Each address of the plurality includes: (1) a nucleic acid (e.g., a DNA or an RNA) encoding a hybrid amino acid sequence which includes a test amino acid sequence and an affinity tag; and, optionally, (2) a binding agent that recognizes the affinity tag. Optionally, each address of the plurality also includes one or both of (i) an RNA polymerase; and (ii) a translation effector.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acids encoding the test amino acid sequences can be obtained from a collection of full-length expressed genes (e.g., a repository of clones), a cDNA library, or a genomic library. The encoding nucleic acids can be nucleic acids (e.g., an mRNA or cDNA) expressed in a tissue, e.g., a normal or diseased tissue. The test polypeptides (i.e., test amino acid sequences) can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second nucleic acids, e.g., a plurality of unique nucleic acids. Hence, the plurality in toto can encode a plurality of test sequences. For example, each address of the plurality can encode a pool of test polypeptide sequences, e.g., a subset of a library or clone bank. A second array can be provided in which each address of the plurality of the second array includes a single or subset of members of the pool present at an address of the first array. The first and the second array can be used consecutively.

In other preferred embodiments, each address of the plurality further includes a second nucleic acid encoding a second amino acid sequence.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth.

These embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

Also featured is a database, e.g., in computer memory or a computer readable medium. Each record of the database can include a field for the amino acid sequence encoded by the nucleic acid sequence and a descriptor or reference for the physical location of the nucleic acid sequence on the array. Optionally, the record also includes a field representing a result (e.g., a qualitative or quantitative result) of detecting the polypeptide encoded by the nucleic acid sequence. The database can include a record for each address of the plurality present on the array. The records can be clustered or have a reference to other records (e.g., including hierarchical groupings) based on the result.

In another aspect, the invention features an array including a substrate having a plurality of addresses. Each address of the plurality includes: (1) an RNA encoding a hybrid amino acid sequence comprising a test amino acid sequence and an affinity tag; and (2) a binding agent that recognizes the affinity tag. Optionally, each address of the plurality also includes one or both of (i) a transcription effector; and (ii) a translation effector.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can further include one or more of: a untranslated leader sequence; a sequence encoding a cleavage site; a recombination site; a 3' untranslated sequence; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acids encoding the test amino acid sequences can be obtained from a collection of full-length expressed genes (e.g., a repository of clones), a cDNA library, or a genomic library. The encoding nucleic acids can be nucleic acids (e.g., an mRNA or cDNA) expressed in a tissue, e.g., a normal or diseased tissue. The test polypeptides (i.e., test amino acid sequences) can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second nucleic acids, e.g., a plurality of unique nucleic acids. Hence, the plurality in toto can encode a plurality of test sequences. For example, each address of the plurality can encode a pool of test polypeptide sequences, e.g., a subset of a library or clone bank. A second array can be provided in which each address of the plurality of the second array includes a single or subset of members of the pool present at an address of the first array. The first and the second array can be used consecutively.

In other preferred embodiments, each address of the plurality further includes a second nucleic acid encoding a second amino acid sequence.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth.

These embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate). In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In still another aspect, the invention features an array including a substrate having a plurality of addresses. Each address of the plurality includes: (1) a polypeptide comprising a test amino acid sequence and an affinity tag; and optionally (2) a binding agent. The binding agent is optimally capable of attaching to the affinity tag of the polypeptide. Optionally, each address of the plurality also includes a translation effector and/or a transcription effector.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence of the polypeptide is identical to all other test amino acid sequences in the plurality of addresses. In a preferred embodiment, the affinity tag of the polypeptide at each address of the plurality is the same, or substantially identical to all other affinity tags in the plurality of addresses.

In a preferred embodiment, the polypeptide has more than one affinity tag. In another embodiment, the polypeptide of an address has an affinity tag that differs from at least one other affinity tag of a polypeptide in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

In another embodiment, each address of the plurality further includes a nucleic acid. The nucleic acid at each address of the plurality encodes the polypeptide. The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

In another embodiment, the polypeptide further includes a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

In another embodiment, the polypeptide includes a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The polypeptide can also include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The test amino acid sequence can further includes a protein splicing sequence or intein. The intein can be inserted in the middle of a test amino acid sequence. The intein can be a naturally-occurring intein or a mutated intein.

A variety of test amino acid sequences can be disposed at different addresses of the plurality. For example, the test amino acid sequences can be polypeptides expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second polypeptides. Hence, the plurality, in toto, can encode a plurality of test polypeptides. For example, each address of the plurality can include a pool of test polypeptide sequences, e.g., a subset of polypeptides encoded by a library or clone bank. A second array can be provided in which each address of the plurality of the second array includes a single or subset of members of the pool present at an address of the first array. The first and the second array can be used consecutively.

In other preferred embodiments, each address of the plurality further includes a second polypeptide.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second test amino acid sequence can include a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. These embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate). In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

Also featured is a database, e.g., in computer memory or a computer readable medium. Each record of the database can include a field for the amino acid sequence of the polypeptide at an address and a descriptor or reference for the physical location of the address on the array. Optionally, the record also includes a field representing a result (e.g., a qualitative or quantitative result) of detecting the polypeptide. The database can include a record for each address of the plurality present on the array. The records can be clustered or have a reference to other records (e.g., including hierarchical groupings) based on the result.

The invention also features a method of providing an array. The method includes: (1) providing a substrate with a plurality of addresses; and (2) providing at each address of the plurality at least (i) a nucleic acid encoding an amino acid sequence comprising a test amino acid sequence and an affinity tag, and optionally (ii) a binding agent that recognizes the affinity tag.

The method can further include contacting each address of the plurality with one or more of (i) a transcription effector, and (ii) a translation effector. Optionally, the substrate is maintained under conditions permissive for the amino acid sequence to bind the binding agent. One or more addresses can then be washed, e.g., to remove at least one of (i) the nucleic acid, (ii) the transcription effector, (iii) the translation effector, and/or (iv) an unwanted polypeptide, e.g., an unbound polypeptide or unfolded polypeptide. The array can optionally be contacted with a compound, e.g., a chaperone; a protease; a protein-modifying enzyme; a small molecule, e.g., a small organic compound (e.g., of molecular weight less than 5000, 3000, 1000, 700, 500, or 300 Daltons); nucleic acids; or other complex macromolecules e.g., complex sugars, lipids, or matrix molecules.

The array can be further processed, e.g., prepared for storage. It can be enclosed in a package, e.g., an air- or water-resistant package. The array can be desiccated, frozen, or contacted with a storage agent (e.g., a cryoprotectant, an anti-bacterial, an anti-fungal). For example, an array can be rapidly frozen after being optionally contacted with a cryoprotectant. This step can be done at any point in the process (e.g., before or after contacting the array with an RNA polymerase; before or after contacting the array with a translation effector; or before or after washing the array). The packaged product can be supplied to a user with or without additional contents, e.g., a transcription effector, a translation effector, a vector nucleic acid, an antibody, and so forth.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acid sequences encoding the test amino acid sequences can be obtained from a collection of full-length expressed genes (e.g., a repository of clones), a cDNA library, or a genomic library. The test amino acid sequences can be genes expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second nucleic acids, e.g., a plurality of unique nucleic acids. Hence, the plurality in toto can encode a plurality of test sequences. For example, each address of the plurality can encode a pool of test polypeptide sequences, e.g., a subset of a library or clone bank. A second array can be provided in which each address of the plurality of the second array includes a single or subset of members of the pool present at an address of the first array. The first and the second array can be used consecutively.

In other preferred embodiments, each address of the plurality further includes a second nucleic acid encoding a second amino acid sequence.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). The method can further include detecting the second test amino acid sequence at each address of the plurality, e.g., by detecting the detectable amino acid sequence (e.g., the epitope tag, enzyme or fluorescent protein).

In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. The method can further include detecting the modification at each address of the plurality.

These embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

The method can further include providing a database, e.g., in computer memory or a computer readable medium. Each record of the database can include a field for the amino acid sequence encoded by the nucleic acid sequence and a descriptor or reference for the physical location of the nucleic acid sequence on the array. The database can include a record for each address of the plurality present on the array. Optionally, the method includes entering into the record also includes a field representing a result (e.g., a qualitative or quantitative result) of detecting the polypeptide encoded by the nucleic acid sequence. The method can also further include clustering or grouping the records based on the result.

The invention also features a method of providing an array to a user. The method includes providing the user with a substrate having a plurality of addresses and a vector nucleic acid. The vector nucleic acid can include one or more sites for insertion of a test amino acid sequence (e.g., a recombination site or a restriction site), and a sequence encoding an affinity tag. In a preferred embodiment, the vector nucleic acid has two sites for insertion, and a toxic gene inserted between the two sites. In another embodiment, the sites for insertion are homologous recombination or site-specific recombination sites, e.g., a lambda att site or variant thereof; a lox site; or a FLP site. In a preferred embodiment, one or both recombination sites lack stop codons in the reading frame of a nucleic acid encoding a test amino acid sequence. In another preferred embodiment, one or both recombination sites include a stop codon in the reading frame of a nucleic acid encoding a test amino acid sequence.

In a much preferred embodiment, the affinity tag is in frame with the translation frame of a nucleic acid sequence (e.g., a sequence to be inserted) encoding a test amino acid sequence. In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence. The cleavage site can be a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

In a preferred embodiment, the method includes providing the user with at least a second vector nucleic acid. The second vector nucleic acid can include one or more sites for insertion of a test amino acid sequence (e.g., a recombination site or a restriction site). In one embodiment, the second vector nucleic acid has a second test amino acid sequence inserted therein. Multiple nucleic acids can be provided, each having a unique test amino acid sequence, e.g., for disposal at a unique address of the substrate. The method can further include contacting each address with a transcription effector and/or a translation effector.

In a preferred embodiment, the second vector nucleic acid has a recognition tag, e.g., an epitope tag, an enzyme, a fluorescent protein (e.g., GFP, BFP, variants thereof).

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses.

The first and/or second vector nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter.

In a preferred embodiment, the method further includes contacting the vector nucleic acid, and optionally the second vector nucleic acid, with a test nucleic acid which includes a nucleic acid encoding a test amino acid sequence so as to insert the test amino acid sequence into the vector nucleic acid. The test nucleic acid can be flanked, e.g., on both ends by a site, e.g., a site compatible with the vector nucleic acid (e.g., having sequence for recombination with a sequence in the vector; or having a restriction site which leaves an overhang or blunt end such that the overhang or blunt end can be ligated into the vector nucleic acid (e.g., the restricted vector nucleic acid)). The contact step can include contacting the vector nucleic acid with a recombinase, a ligase, and/or a restriction endonuclease. For example, the recombinase can mediate recombination, e.g., site-specific recombination or homologous recombination, between a recombination site on the test nucleic acid and a recombination sequence on the vector nucleic acid.

In a preferred embodiment, each address of the plurality has a binding agent capable of recognizing the affinity tag. The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In a preferred embodiment, the method further includes disposing at an address of the plurality a vector nucleic acid that includes a nucleic acid encoding a test amino acid sequence. This step can be repeated until a vector nucleic acid is disposed at each address of the plurality. In embodiments using a second vector nucleic acid in addition to the first, the method can include disposing at each address of the plurality a second vector nucleic acid encoding a different test amino acid sequence from the first vector nucleic acid.

In another preferred embodiment, the method further includes disposing at an address of the plurality a vector nucleic acid that does not include a nucleic acid encoding a test amino acid sequence and concurrently or separately disposing a nucleic acid encoding a test amino acid sequence. This step can be repeated until a vector nucleic acid is disposed at each address of the plurality. The method can also further including contacting each address of the plurality with a recombinase or a ligase.

The first or second vector nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The first or second vector nucleic acid sequence can further include a sequence encoding a protein splicing sequence or intein. The intein can be inserted in the middle of a test amino acid sequence. The intein can be a naturally-occurring intein or a mutated intein.

The nucleic acids encoding the test amino acid sequences can be obtained from a collection of full-length expressed genes (e.g., a repository of clones), a cDNA library, or a genomic library. The encoding nucleic acids can be nucleic acids (e.g., an mRNA or cDNA) expressed in a tissue, e.g., a normal or diseased tissue. The test polypeptides (i.e., test amino acid sequences) can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

The method can further include detecting the first or the second test amino acid sequence at each address of the plurality.

In another preferred embodiment using a first and a second vector nucleic acid, one test amino acid sequence is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. The method can further include detecting the modification at each address of the plurality.

These embodiments can be used to identify an interaction or to identify a compound that modulates, e.g., inhibits or enhances, an interaction.

In another aspect, the invention features a method of providing an array of polypeptides. The method includes: (1) providing or obtaining a substrate with a plurality of addresses, each address of the plurality including (i) a nucleic acid encoding an amino acid sequence comprising a test amino acid sequence and an affinity tag, and (ii) a binding agent that recognizes the affinity tag; (2) contacting each address of the plurality with a translation effector to thereby translate the hybrid amino acid sequence; and (3) maintaining the substrate under conditions permissive for the amino acid sequence to bind the binding agent.

In one embodiment, the nucleic acid provided on the substrate is synthesized in situ, e.g., by light-directed chemistry. In another embodiment, each address of the plurality is provided with a nucleic acid, e.g., by pipetting, spotting, printing (e.g., with pins), piezoelectric delivery, or, e.g., other means of mechanical delivery. In a preferred embodiment, the provided nucleic acid is a template nucleic acid, and the method further includes amplifying the template, e.g., by PCR, NASBA, or RCA. The method can further include transcribing the nucleic acid to produce one or more RNA molecules encoding the test amino acid sequence.

The method can further include washing the substrate, e.g., after sufficient contact with a translation effector. The wash step can be repeated, e.g., one or more times, e.g., until a translation effector or translation effector component is removed. The wash step can remove unbound proteins. The stringency of the wash step can vary, e.g., the salt, pH, and buffer composition of the wash buffer can vary. For example, if the translated test polypeptide is covalently captured, or captured by an interaction resistant to chaotropes (e.g., binding of a 6-histidine motif to $Ni^{2+}$ NTA), the substrate can be washed with a chaotrope, (e.g., guanidinium hydrochloride, or urea). In a subsequent step, the chaotrope can itself be washed from the array, and the polypeptides renatured.

In one embodiment, the nucleic acid sequence also encodes a cleavage site, e.g., a protease site, e.g., between the test amino acid sequence and the affinity tag. The method can further include contacting an address of the array with a protease that specifically recognizes the site.

The method can further include contacting the substrate with a second substrate. For example, in an embodiment wherein the substrate is a gel, the gel can be contacted with a second gel, and the contents of one gel can be transferred to another (e.g., by diffusion or electrophoresis). The method can include disrupting the binding between the affinity tag and the binding agent or between the binding agent and the substrate prior to transfer.

The method can further include contacting the substrate with living cells, and detecting an address wherein a parameter of the cell is altered relative to another address.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for i recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acid sequences encoding the test amino acid sequences can be obtained from a collection of full-length expressed genes (e.g., a repository of clones), a cDNA library, or a genomic library. The test amino acid sequences can be genes expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second nucleic acids, e.g., a plurality of unique nucleic acids. Hence, the plurality in toto can encode a plurality of test sequences. For example, each address of the plurality can encode a pool of test polypeptide sequences, e.g., a subset of a library or clone bank. A second array can be provided in which each address of the plurality of the second array includes a single or subset of members of the pool present at an address of the first array. The first and the second array can be used consecutively.

In other preferred embodiments, each address of the plurality further includes a second nucleic acid encoding a second amino acid sequence.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). The method can further include detecting the second test amino acid sequence at each address of the plurality, e.g., by detecting the detectable amino acid sequence (e.g., the epitope tag, enzyme or fluorescent protein).

In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. The method can further include detecting the modification at each address of the plurality.

These embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate). In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In another aspect, the invention features a method of evaluating, e.g., identifying a polypeptide-polypeptide interaction. The method includes: (1) providing or obtaining a substrate with a plurality of addresses, each address of the plurality comprising (i) a first nucleic acid encoding an amino acid sequence comprising a first amino acid sequence and an affinity tag, (ii) a binding agent that recognizes the affinity tag, and (iii) a second nucleic acid encoding a second amino acid sequence; (2) contacting each address of the plurality with a translation effector to thereby translate the first nucleic acid and the second nucleic acid to synthesize the first and second amino acid sequences; and optionally (3) maintaining the substrate under conditions permissive for the hybrid amino acid sequence to bind binding agent.

In one preferred embodiment, the first amino acid sequence is common to all addresses of the plurality, and a second test amino acid sequence is unique among all the addresses of the plurality. For example, the second test amino acid sequences can be query sequences whereas the first amino test amino acid sequence can be a target sequence. In another preferred embodiment, the first amino acid sequence is unique among all the addresses of the plurality, and the second amino acid sequence is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

The method can further include detecting the presence of the second amino acid sequence at each of the plurality of addresses.

In one preferred embodiment, the second nucleic acid sequence also encodes a polypeptide tag. The polypeptide tag can be an epitope (e.g., recognized by a monoclonal antibody), or a binding agent (e.g., avidin or streptavidin, GST, or chitin binding protein). The detection of the second amino acid sequence can entail contacting each address of the plurality with a binding agent, e.g., a labeled biotin moiety, labeled glutathione, labeled chitin, a labeled antibody, etc. In another embodiment, each address of the plurality is contacted with an antibody specific to the second amino acid sequence.

In another preferred embodiment, the second nucleic acid sequence includes a recognition tag. The recognition tag can be an epitope tag, enzyme or fluorescent protein. Examples of enzymes include horseradish peroxidase, alkaline phosphatase, luciferase, or cephalosporinase. The method can further include contacting each address of the plurality with an appropriate cofactor and/or substrate for the enzyme. Examples of fluorescent proteins include green fluorescent protein (GFP), and variants thereof, e.g., enhanced GFP, blue fluorescent protein (BFP), cyan FP, etc. The detection of the second amino acid sequence can entail monitoring fluorescence, assessing enzyme activity, measuring an added binding agent, e.g., a labeled biotin moiety, a labeled antibody, etc.

In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. The method can further include detecting the modification at each address of the plurality.

These embodiments can be used to identify an interaction or to identify a compound that modulates, e.g., inhibits or enhances, an interaction. For example, the method can further include contacting each address of the plurality with a compound, e.g., a small organic molecule, a polypeptide, or a nucleic acid to thereby determine if the compound alters the interaction between the first and second amino acid.

In one preferred embodiment, the first amino acid sequence is a drug candidate, e.g. a random peptide, a randomized or mutated scaffold protein, or a secreted protein (e.g., a cell surface protein, an ectodomain of a transmembrane protein, an antibody, or a polypeptide hormone); and the second amino acid sequence is a drug target. A first amino acid sequence at an address where an interaction between the first amino acid sequence and the second amino acid is detected can be used as a candidate amino acid sequence for additional refinement or as a drug. The first amino acid sequence can be administered to a subject. A nucleic acid encoding the first amino acid sequence can be administered to a subject. In a related preferred embodiment, the first amino acid sequence is the drug target, and the second amino acid sequence is the drug candidate.

In a preferred embodiment, each first amino acid sequence in the plurality of addresses is unique. For example, a first amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the first amino acid sequence encoded by the nucleic acid at each address of the plurality is identical to all other first amino acid sequences in the plurality of addresses. In a preferred embodiment, the affinity tag encoded by the first nucleic acid at each address of the plurality is the same, or substantially identical to all other affinity tags in the plurality of addresses. In another preferred embodiment, the first nucleic acid at each address of the plurality encodes more than one affinity tag. In yet another preferred embodiment, the affinity tag encoded by the first nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The first and/or second nucleic acid can be a RNA, or a DNA (e.g., a single-stranded DNA, or a double stranded DNA). In a preferred embodiment, the first and/or second nucleic acid includes a plasmid DNA or a fragment thereof; an amplification product (e.g., a product generated by RCA, PCR, NASBA); or a synthetic DNA.

The first and/or second nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the first and/or second nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the first and/or second nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The first nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The first and/or second nucleic acid sequence can further include an identifier sequence, e.g., a non-coding nucleic acid sequence, e.g., one that is synthetically inserted and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The first and/or second amino acid sequence can further include a protein splicing sequence or intein. The intein can be inserted in the middle of a test amino acid sequence. The intein can be a naturally-occurring intein or a mutated intein.

The first and/or second nucleic acid sequences encoding the first and/or second amino acid sequences can be obtained from a collection of full-length expressed genes (e.g., a repository of clones), a cDNA library, or a genomic library. The first and/or second nucleic acid sequences can be nucleic acids expressed in a tissue, e.g., a normal or diseased tissue. The first and/or second amino acid sequences can be mutants or variants of a scaffold protein (e.g., an antibody, zinc-finger, polypeptide hormone etc.). In yet another embodiment, they are random amino acid sequences, patterned amino acids sequences, or designed amino acids sequences (e.g., sequence designed by manual, rational, or computer-aided approaches).

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In another aspect, the invention features a method of evaluating, e.g., identifying a polypeptide-polypeptide interaction. The method includes: (1) providing or obtaining an array made by the following process: (A) providing or obtaining a substrate with a plurality of addresses, each address having a binding agent that recognizes an affinity tag; (B) disposing in or on each address of the plurality (i) a first nucleic acid encoding an amino acid sequence comprising a first amino acid sequence and the affinity tag, and (ii) a second nucleic acid encoding a second amino acid sequence; and, optionally, (C) contacting each address of the plurality with a translation effector to thereby translate the first and second nucleic acid.

The method can further include maintaining the substrate under conditions permissive for the hybrid amino acid sequence to bind binding agent. The method can further include detecting the presence of the second amino acid sequence at each of the plurality of addresses.

In one preferred embodiment, the first amino acid sequence is common to all addresses of the plurality, and a second test amino acid sequence is unique among all the addresses of the plurality. For example, the second test amino acid sequences can be query sequences whereas the first amino test amino acid sequence can be a target sequence. In another preferred embodiment, the first amino acid sequence is unique among all the addresses of the plurality, and the second amino acid sequence is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

The method can further include detecting the presence of the second amino acid sequence at each of the plurality of addresses.

In one preferred embodiment, the second nucleic acid sequence also encodes a polypeptide tag. The polypeptide tag can be an epitope (e.g., recognized by a monoclonal antibody), or a binding agent (e.g., avidin or streptavidin, GST, or chitin binding protein). The detection of the second amino acid sequence can entail contacting each address of the plurality with a binding agent, e.g., a labeled biotin moiety, labeled glutathione, labeled chitin, a labeled antibody, etc. In another embodiment, each address of the plurality is contacted with an antibody specific to the second amino acid sequence.

In another preferred embodiment, the second nucleic acid sequence includes a recognition tag. The recognition tag can be an epitope tag, enzyme or fluorescent protein. Examples of enzymes include horseradish peroxidase, alkaline phosphatase, luciferase, or cephalosporinase. The method can further include contacting each address of the plurality with an appropriate cofactor and/or substrate for the enzyme. Examples of fluorescent proteins include green fluorescent protein (GFP), and variants thereof, e.g., enhanced GFP, blue fluorescent protein (BFP), cyan FP, etc. The detection of the second amino acid sequence can entail monitoring fluorescence, assessing enzyme activity, measuring an added binding agent, e.g., a labeled biotin moiety, a labeled antibody, etc.

In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth. The method can further include detecting the modification at each address of the plurality.

These embodiments can be used to identify an interaction or to identify a compound that modulates, e.g., inhibits or enhances, an interaction. For example, the method can further include contacting each address of the plurality with a compound, e.g., a small organic molecule, a polypeptide, or a nucleic acid to thereby determine if the compound alters the interaction between the first and second amino acid.

In one preferred embodiment, the first amino acid sequence is a drug candidate, e.g. a random peptide, a randomized or mutated scaffold protein, or a secreted protein (e.g., a cell surface protein, an ectodomain of a transmembrane protein, an antibody, or a polypeptide hormone); and the second amino acid sequence is a drug target. A first amino acid sequence at an address where an interaction between the first amino acid sequence and the second amino acid is detected can be used as a candidate amino acid sequence for additional refinement or as a drug. The first amino acid sequence can be administered to a subject. A nucleic acid encoding the first amino acid sequence can be administered to a subject. In a related preferred embodiment, the first amino acid sequence is the drug target, and the second amino acid sequence is the drug candidate.

In a preferred embodiment, each first amino acid sequence in the plurality of addresses is unique. For example, a first amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the first amino acid sequence encoded by the nucleic acid at each address of the plurality is identical to all other first amino acid sequences in the plurality of addresses. In a preferred embodiment, the affinity tag encoded by the first nucleic acid at each address of the plurality is the same, or substantially identical to all other affinity tags in the plurality of addresses. In another preferred embodiment, the first nucleic acid at each address of the plurality encodes more than one affinity tag. In yet another preferred embodiment, the affinity tag encoded by the first nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The first and/or second nucleic acid can be a RNA, or a DNA (e.g., a single-stranded DNA, or a double stranded DNA). In a preferred embodiment, the first and/or second nucleic acid includes a plasmid DNA or a fragment thereof; an amplification product (e.g., a product generated by RCA, PCR, NASBA); or a synthetic DNA.

The first and/or second nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the first and/or second nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the first and/or second nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The first nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The first and/or second nucleic acid sequence can further include an identifier sequence, e.g., a non-coding nucleic acid sequence, e.g., one that is synthetically inserted and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The first and/or second amino acid sequence can further include a protein splicing sequence or intein. The intein can be inserted in the middle of a test amino acid sequence. The intein can be a naturally-occurring intein or a mutated intein.

The first and/or second nucleic acid sequences encoding the first and/or second amino acid sequences can be obtained from a collection of full-length expressed genes (e.g., a repository of clones), a cDNA library, or a genomic library. The first and/or second nucleic acid sequences can be nucleic acids expressed in a tissue, e.g., a normal or diseased tissue. The first and/or second amino acid sequences can be mutants or variants of a scaffold protein (e.g., an antibody, zinc-finger, polypeptide hormone etc.). In yet another embodiment, they are random amino acid sequences, patterned amino acids sequences, or designed amino acids sequences (e.g., sequence designed by manual, rational, or computer-aided approaches).

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In another aspect, the method features a method of evaluating, e.g., identifying, a polypeptide-polypeptide interaction. The method includes: (1) providing or obtaining an array made by the following production method: (A) providing or obtaining a substrate with a plurality of addresses, each address of the plurality comprising (i) a first nucleic acid encoding a hybrid amino acid sequence comprising a first amino acid sequence and an affinity tag, (ii) a binding agent that recognizes the affinity tag, and (iii) a second nucleic acid encoding a second amino acid sequence; and (B) contacting each address of the plurality with a translation effector to thereby translate the first and second nucleic acid sequences. The evaluation method further includes: (2) at each of the plurality of addresses, detecting at least one parameter selected from the group consisting of: (i) the proximity of the second amino acid sequence to the first amino acid sequence; (ii) the proximity of the second amino acid sequence to the substrate or a compound bound thereto; (iii) the rotational freedom of the second amino acid sequence; and (iv) the refractive index of the substrate. The evaluation method can optionally include, e.g., prior to the detecting step, (3) maintaining the substrate under conditions permissive for the hybrid amino acid sequence to bind binding agent.

The method can further include washing the substrate prior to the detection step. The stringency of the wash step can be adjusted in order to remove the translation effector, and non-specifically bound proteins.

In one preferred embodiment, the first amino acid sequence is common to all addresses of the plurality, and a second test amino acid sequence is unique among all the addresses of the plurality. For example, the second test amino acid sequences can be query sequences whereas the first amino test amino acid sequence can be a target sequence. In another preferred embodiment, the first amino acid sequence is unique among all the addresses of the plurality, and the second amino acid sequence is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

The method can further include detecting the presence of the second amino acid sequence at each of the plurality of addresses.

In one preferred embodiment, the second nucleic acid sequence also encodes a polypeptide tag. The polypeptide tag can be an epitope (e.g., recognized by a monoclonal antibody), or a binding agent (e.g., avidin or streptavidin, GST, or chitin binding protein). The detection of the second amino acid sequence can entail contacting each address of the plurality with a binding agent, e.g., a labeled biotin moiety, labeled glutathione, labeled chitin, a labeled antibody, etc. In another embodiment, each address of the plurality is contacted with an antibody specific to the second amino acid sequence. The antibody can be labeled, e.g., with a fluorophore.

In another preferred embodiment, the second nucleic acid sequence includes a recognition tag. The recognition tag can be an epitope tag, enzyme or fluorescent protein. Examples of enzymes include horseradish peroxidase, alkaline phosphatase, luciferase, or cephalosporinase. The method can further include contacting each address of the plurality with an appropriate cofactor and/or substrate for the enzyme. Examples of fluorescent proteins include green fluorescent protein (GFP), and variants thereof, e.g., enhanced GFP, blue fluorescent protein (BFP), cyan FP, etc.

The method can further include contacting each address of the plurality with a compound, e.g., a small organic molecule, a polypeptide, or a nucleic acid to thereby determine if the compound alters the interaction between the first and second amino acid.

In one preferred embodiment, the first amino acid sequence is a drug candidate, e.g. a random peptide, a randomized or mutated scaffold protein, or a secreted protein (e.g., a cell surface protein, an ectodomain of a transmembrane protein, an antibody, or a polypeptide hormone); and the second amino acid sequence is a drug target. A first amino acid sequence at an address where an interaction between the first amino acid sequence and the second amino acid is detected can be used as a candidate amino acid sequence for additional refinement or as a drug. The first amino acid sequence can be administered to a subject. A nucleic acid encoding the first amino acid sequence can be administered to a subject. In a related preferred embodiment, the first amino acid sequence is the drug target, and the second amino acid sequence is the drug candidate.

In a preferred embodiment, each first amino acid sequence in the plurality of addresses is unique. For example, a first amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the first amino acid sequence encoded by the nucleic acid at each address of the plurality is identical to all other first amino acid sequences in the plurality of addresses. In a preferred embodiment, the affinity tag encoded by the first nucleic acid at each address of the plurality is the same, or substantially identical to all other affinity tags in the plurality of addresses. In another preferred embodiment, the first nucleic acid at each address of the plurality encodes more than one affinity tag. In yet another preferred embodiment, the affinity tag encoded by the first nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The first and/or second nucleic acid can be a RNA, or a DNA (e.g., a single-stranded DNA, or a double stranded DNA). In a preferred embodiment, the first and/or second nucleic acid includes a plasmid DNA or a fragment thereof; an amplification product (e.g., a product generated by RCA, PCR, NASBA); or a synthetic DNA.

The first and/or second nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the first and/or second nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the first and/or second nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The first nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The first and/or second nucleic acid sequence can further include an identifier sequence, e.g., a non-coding nucleic acid sequence, e.g., one that is synthetically inserted and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The first and/or second amino acid sequence can further include a protein splicing sequence or intein. The intein can be inserted in the middle of a test amino acid sequence. The intein can be a naturally-occurring intein or a mutated intein.

The first and/or second nucleic acid sequences encoding the first and/or second amino acid sequences can be obtained from a collection of full-length expressed genes (e.g., a repository of clones), a cDNA library, or a genomic library. The first and/or second nucleic acid sequences can be nucleic acids expressed in a tissue, e.g., a normal or diseased tissue. The first and/or second amino acid sequences can be mutants or variants of a scaffold protein (e.g., an antibody, zinc-finger, polypeptide hormone etc.). In yet another embodiment, they are random amino acid sequences, patterned amino acids sequences, or designed amino acids sequences (e.g., sequence designed by manual, rational, or computer-aided approaches).

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate). In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In another aspect the invention features a method of identifying an enzyme substrate or cofactor. The method includes: (1) providing a substrate with a plurality of addresses, each address of the plurality comprising (i) a first nucleic acid encoding a hybrid amino acid sequence comprising a first amino acid sequence and an affinity tag, (ii) a binding agent that recognizes the affinity tag and is attached to the substrate, and (iii) a second nucleic acid encoding an enzyme; (2) contacting each address of the plurality with a translation effector to thereby translate the first and second nucleic acid sequences; (3) maintaining the substrate under conditions permissive for the hybrid amino acid sequence to bind binding agent and for activity of the enzyme; (4) detecting the activity of the enzyme at each address of the plurality.

In one embodiment, the first amino acid sequence varies among the addresses of the plurality. In another embodiment, the second nucleic acid varies among the addresses of the plurality. The method can further include contacting each address of the plurality with an enzyme substrate (e.g., radioactive or otherwise labeled such as with ATP, GTP, s-adenosylmethionine, ubiquitin, and so forth) or a cofactor, e.g., NADH, NADPH, FAD. A substrate or cofactor can be provided with the translation effector.

The detecting step can include monitoring a protein bound by the labeled binding agent (radioactive or otherwise), e.g., after a wash step. The label can be present in solution (e.g., as a cofactor or reaction substrate) and can be transferred to first amino acid sequence by the enzyme, e.g., such that the label is covalently attached to the first amino acid sequence (e.g., such as in phosphorylation). The label can be present in solution and can be bound to the first amino acid sequence (e.g., non-covalently) as a result of an enzyme catalyzed or assisted reaction (e.g., the enzyme can effect a conformational change in the first amino acid sequence, such as a GTP exchange factor protein acting on a GTP binding protein).

In one preferred embodiment, the first amino acid sequence is common to all addresses of the plurality, and a second test amino acid sequence is unique among all the addresses of the plurality. For example, the second test amino acid sequences can be query sequences whereas the first amino test amino acid sequence can be a target sequence. In another preferred embodiment, the first amino acid sequence is unique among all the addresses of the plurality, and the second amino acid sequence is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

In a preferred embodiment, each first amino acid sequence in the plurality of addresses is unique. For example, a first amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the first amino acid sequence encoded by the nucleic acid at each address of the plurality is identical to all other first amino acid sequences in the plurality of addresses. In a preferred embodiment, the affinity tag encoded by the first nucleic acid at each address of the plurality is the same, or substantially identical to all other affinity tags in the plurality of addresses. In another preferred embodiment, the first nucleic acid at each address of the plurality encodes more than one affinity tag. In yet another preferred embodiment, the affinity tag encoded by the first nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The first and/or second nucleic acid can be a RNA, or a DNA (e.g., a single-stranded DNA, or a double stranded DNA). In a preferred embodiment, the first and/or second nucleic acid includes a plasmid DNA or a fragment thereof; an amplification product (e.g., a product generated by RCA, PCR, NASBA); or a synthetic DNA.

The first and/or second nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the first and/or second nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the first and/or second nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The first nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The first and/or second nucleic acid sequence can further include an identifier sequence, e.g., a non-coding nucleic acid sequence, e.g., one that is synthetically inserted and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The first and/or second amino acid sequence can further include a protein splicing sequence or intein. The intein can be inserted in the middle of a test amino acid sequence. The intein can be a naturally-occurring intein or a mutated intein.

The first and/or second nucleic acid sequences encoding the first and/or second amino acid sequences can be obtained from a collection of full-length expressed genes (e.g., a repository of clones), a cDNA library, or a genomic library. The first and/or second nucleic acid sequences can be nucleic acids expressed in a tissue, e.g., a normal or diseased tissue. The first and/or second amino acid sequences can be mutants or variants of a scaffold protein (e.g., an antibody, zinc-finger, polypeptide hormone etc.). In yet another embodiment, they are random amino acid sequences, patterned amino acids sequences, or designed amino acids sequences (e.g., sequence designed by manual, rational, or computer-aided approaches).

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate). In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

In another aspect, the invention features a method of producing a protein-interaction map for a plurality of amino acid sequences. The method includes: (1) providing (i) a first plurality of nucleic acid sequences, each encoding an amino acid sequence comprising an amino acid sequence of the plurality of amino acid sequences and an affinity tag; (ii) a second plurality of nucleic acid, each encoding an amino acid sequence comprising an amino acid sequence of the plurality of amino acid sequences and recognition tag; and (iii) a substrate with a plurality of addresses and a binding agent that binds the affinity tag and is attached to the substrate; (2) disposing on the substrate, at each address of the plurality of addresses, a nucleic acid of the first plurality and a nucleic acid of the second plurality; (3) contacting each address of the plurality of addresses with a translation effector to thereby translate the first and second nucleic acid sequences; (4) maintaining the substrate under conditions permissive for the affinity tag to bind binding agent; (5) optionally washing the substrate to remove the translation effector and unbound polypeptides; and (6) detecting the recognition tag at each address of the plurality.

In a preferred embodiment, all possible pairs of amino acid sequences from the plurality of amino acid sequences are present on the array.

Also featured is a database, e.g., in computer memory or a computer readable medium. Each record of the database can include a field for the amino acid sequence encoded by the first nucleic acid sequence, a field for the amino acid sequence encoded by the second nucleic acid sequence, and a field representing the result (e.g., a qualitative or quantitative result) of detecting the recognition tag in the aforementioned method. The database can include a record for each address of the plurality present on the array. Further the database can include a descriptor or reference for the physical location of the nucleic acid sequence on the array. The records can be clustered or have a reference to other records (e.g., including hierarchical groupings) based on the result.

Also featured is a method of providing tagged polypeptides. The method includes: (1) providing a substrate with a plurality of addresses, each address of the plurality comprising (i) a nucleic acid encoding an amino acid sequence comprising a test amino acid sequence and an affinity tag, and (ii) a particle attached to a binding agent that recognizes the affinity tag; (2) contacting each address of the plurality with a translation effector to thereby translate the amino acid sequence; and (3) maintaining the substrate under conditions permissive for the amino acid sequence to contact the binding agent.

In one preferred embodiment, the nucleic acid sequence is also attached to the particle.

In another preferred embodiment, the particle, e.g., a bead or nanoparticle, further contains information encoding its identity, e.g., a reference to the address on which it is disposed. The particle can be tagged using a chemical tag, or an electronic tag (e.g., a transponder). The particles can be disposed on the substrate such that they can be removed for later analysis. In one embodiment, multiple particles with the same identifier are disposed at each address of the plurality. The particles can be collected after translation and attachment of the amino acid sequence. The particles can then be subdivided into aliquots. A particle with a given property, e.g., the ability to bind a labeled compound can be identified. The identity of the particle can be determined to thereby identify the amino acid sequence attached to the particle.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acid sequences encoding the test amino acid sequences can be obtained from a collection of full-length expressed genes (e.g., a repository of clones), a cDNA library, or a genomic library. The test amino acid sequences can be genes expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In another aspect, the invention features a method of providing tagged polypeptides. The method includes: providing a substrate with a plurality of addresses, each address of the plurality having a nucleic acid (i) encoding an amino acid sequence comprising: (1) a test amino acid sequence, and (2) a tag; and (ii) a handle; contacting each address of the plurality with a translation effector to thereby translate the nucleic acid sequence; and maintaining the substrate under conditions permissive for the tag to contact the handle to thereby form a complex of the nucleic acid and the test polypeptide having the test amino acid sequence.

In one embodiment, the handle is biotin, and the tag is avidin. For example, the nucleic acid has a biotin covalent attached to a nucleotide. The nucleic acid can be formed by amplification of a template nucleic acid using a synthetic oligonucleotide having a biotin moiety covalently attached at its 5' end. In another embodiment, the handle is glutathione, and the tag is glutathione-S-transferase. For example, the nucleic acid has a glutathione moiety covalent attached to a nucleotide. The nucleic acid can be formed by amplification of a template nucleic acid using a synthetic oligonucleotide having a biotin moiety covalently attached at its 5' end.

In one embodiment, the handle includes a keto group, and the tag is a hydrazine. A covalent bond is formed between the handle and tag.

The method can further includes combining the complexes formed at all the addresses into a pool, selecting a polypeptide from the pool, and amplifying the complexed nucleic acid sequence to thereby identify the selected amino acid sequence.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the tag is fused directly to the test amino acid sequence, e.g., directly amino-terminal, or directly carboxy-terminal. In another preferred embodiment, the tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and tag can be amino-terminal or carboxy-terminal to the test amino acid sequence.

The nucleic acid can be an RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the first tag. The second tag can be C-terminal to the test amino acid sequence and the first tag can be N-terminal to the test amino acid sequence; the second tag can be N-terminal to the test amino acid sequence, and the first tag can be C-terminal to the test amino acid sequence; the second tag and the first tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acid sequences encoding the test amino acid sequences can be obtained from a collection of full-length expressed genes (e.g., a repository of clones), a cDNA library, or a genomic library. The test amino acid sequences can be genes expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

The handle can be attached to the substrate. For example, the substrate can be derivatized and the handle covalent attached thereto. The handle can be attached via a bridging moiety, e.g., a specific binding pair. (e.g., the substrate contains a first member of a specific binding pair, and the handle is linked to the second member of the binding pair, the second member being attached to the substrate).

In yet another embodiment, an insoluble substrate (e.g., a bead or particle), is disposed at each address of the plurality, and the handle is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

The invention also features a kit which includes: (1) an array comprising a plurality of addresses, wherein each address of the plurality comprises a handle and (2) a vector nucleic acid comprising (i) a promoter; (ii) an entry site; and (iii) a tag encoding sequence, wherein the tag can be attached to the handle.

The vector nucleic acid can include one or more sites for insertion of a test amino acid sequence (e.g., a recombination site or a restriction site), and a sequence encoding an tag. In a preferred embodiment, the vector nucleic acid has two sites for insertion, and a toxic gene inserted between the two sites. In another embodiment, the sites for insertion are homologous recombination or site-specific recombination sites, e.g., a lambda att site or variant thereof; a lox site; or a FLP site. In a preferred embodiment, one or both recombination sites lack stop codons in the reading frame of a nucleic acid encoding a test amino acid sequence. In another preferred embodiment, one or both recombination sites include a stop codon in the reading frame of a nucleic acid encoding a test amino acid sequence.

In a much preferred embodiment, the tag is in frame with the translation frame of a nucleic acid sequence (e.g., a sequence to be inserted) encoding a test amino acid sequence. In a preferred embodiment, the tag is fused directly to the test amino acid sequence, e.g., directly amino-terminal, or directly carboxy-terminal. In another preferred embodiment, the tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and tag can be amino-terminal or carboxy-terminal to the test amino acid sequence. The cleavage site can be a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

In one embodiment, the handle includes a keto group, and the tag is a hydrazine. A covalent bond is formed between the handle and tag. The kit can further include an unnatural amino acid having a keto group, e.g., a reactable keto group on a side chain. The kit can also further include a tRNA, and optionally a tRNA synthetase for amino-acylating the tRNA with the unnatural amino acid. The tRNA can be a stop codon suppressing tRNA.

In a preferred embodiment, the kit also includes at least a second vector nucleic acid. The second vector nucleic acid can include one or more sites for insertion of a test amino acid sequence (e.g., a recombination site or a restriction site).

In another embodiment, the kit also includes multiple nucleic acids encoding unique test amino acid sequences. These encoding nucleic acids can be flanked, e.g., on both ends by a site, e.g., a site compatible with the vector nucleic acid (e.g., having sequence for recombination with a sequence in the vector; or having a restriction site which leaves an overhang or blunt end such that the overhang or blunt end can be ligated into the vector nucleic acid (e.g., the restricted vector nucleic acid)).

In another preferred embodiment, the kit also includes a transcription effector and/or a translation effector.

In a preferred embodiment, the second vector nucleic acid has a recognition tag, e.g., an epitope tag, an enzyme, a fluorescent protein (e.g., GFP, BFP, variants thereof).

The first and/or second vector nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter.

In a preferred embodiment, the kit also includes a recombinase, a ligase, and/or a restriction endonuclease. For example, the recombinase can mediate recombination, e.g., site-specific recombination or homologous recombination, between a recombination site on the test nucleic acid and a recombination sequence on the vector nucleic acid. For example, the recombinase can be lambda integrase, HIV integrase, Cre, or FLP recombinase.

In a preferred embodiment, each address of the plurality has a handle capable of recognizing the tag. The handle can be attached to the substrate. For example, the substrate can be derivatized and the handle covalent attached thereto. The handle can be attached via a bridging moiety, e.g., a specific binding pair. (e.g., the substrate contains a first member of a specific binding pair, and the handle is linked to the second member of the binding pair, the second member being attached to the substrate).

In yet another embodiment, the array of the kit includes an insoluble substrate (e.g., a bead or particle), disposed at each address of the plurality, and the handle is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

The first or second vector nucleic acid can include a sequence encoding a second polypeptide tag in addition to the tag. The second tag can be C-terminal to the test amino acid sequence and the tag can be N-terminal to the test amino acid sequence; the second tag can be N-terminal to the test amino acid sequence, and the tag can be C-terminal to the test amino acid sequence; the second tag and the tag can be adjacent to one another, or separated by a linker sequence, both being N-terminal or C-terminal to the test amino acid sequence. In one embodiment, the second tag is an additional tag, e.g., the same or different from the first tag. In another embodiment, the second tag is a recognition tag. For example, the recognition tag can report the presence and/or amount of test polypeptide at an address. Preferably the recognition tag has a sequence other than the sequence of the tag. In still another embodiment, a plurality of polypeptide tags (e.g., less than 3, 4, 5, about 10, or about 20 tags) are encoded in addition to the first tag. Each polypeptide tag of the plurality can be the same as or different from the first tag.

The first or second vector nucleic acid sequence can further include a sequence encoding a protein splicing sequence or intein. The intein can be inserted in the middle of a test amino acid sequence. The intein can be a naturally-occurring intein or a mutated intein.

The nucleic acids encoding the test amino acid sequences can be obtained from a collection of full-length expressed genes (e.g., a repository of clones), a cDNA library, or a genomic library. The encoding nucleic acids can be nucleic acids (e.g., an mRNA or cDNA) expressed in a tissue, e.g., a normal or diseased tissue. The test polypeptides (i.e., test amino acid sequences) can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

The kit can further include software and/or a database, e.g., in computer memory or a computer readable medium (e.g., a CD-ROM, a magnetic disc, flash memory. Each record of the database can include a field for the test amino acid sequence encoded by the nucleic acid sequence and a descriptor or reference for the physical location of the encoding nucleic acid sequence in the kit, e.g., location in a microtitre plate. Optionally, the record also includes a field representing a result (e.g., a qualitative or quantitative result) of detecting the polypeptide encoded by the nucleic acid sequence. The database can include a record for each address of the plurality present on the array. The records can be clustered or have a reference to other records (e.g., including hierarchical groupings) based on the result. The software can contain computer readable code to configure a computer-controlled robotic apparatus to manipulate nucleic acids encoding test amino acid sequences and vector nucleic acids in order to insert the encoding nucleic acids into the vector nucleic acids and further to manipulate the insertion products onto addresses of the array.

The kit can also include instructions for use of the array or a link or indication of a network resource (e.g., a web site) having instructions for use of the array or the above database of records describing the addresses of the array.

A method of providing an array includes providing the aforementioned kit, and a plurality of nucleic acid sequences, each encoding a unique test amino acid sequence and an excision site. The method further includes removing each of the plurality of nucleic acid sequence from the excision site and inserting it into the entry site of the vector nucleic acid to thereby generate a test nucleic acid sequence encoding a test polypeptide comprising the test amino acid sequence and the tag; and disposing each of the plurality of test nucleic acid sequences at an address of the array.

Another featured kit includes: an array comprising a substrate having a plurality of addresses, wherein each address of the plurality comprises a handle, and a nucleic acid sequence encoding an amino acid sequence comprising: (a) a test amino acid sequence, and (b) a tag. The kit can optionally further include at least one of: a translation effector and a transcription effector.

The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The nucleic acid sequence can further include a sequence encoding a protein splicing sequence or intein. The intein can be inserted in the middle of a test amino acid sequence. The intein can be a naturally-occurring intein or a mutated intein.

The nucleic acids encoding the test amino acid sequences can be obtained from a collection of full-length expressed genes (e.g., a repository of clones), a cDNA library, or a genomic library. The encoding nucleic acids can be nucleic acids (e.g., an mRNA or cDNA) expressed in a tissue, e.g., a normal or diseased tissue. The test polypeptides (i.e., test amino acid sequences) can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the test amino acid sequences on half the addresses of an array are from a diseased tissue or a first species, whereas the sequences on the remaining half are from a normal tissue or a second species.

In a preferred embodiment, each address of the plurality further includes one or more second nucleic acids, e.g., a plurality of unique nucleic acids. Hence, the plurality in toto can encode a plurality of test sequences. For example, each address of the plurality can encode a pool of test polypeptide sequences, e.g., a subset of a library or clone bank. A second array can be provided in which each address of the plurality of the second array includes a single or subset of members of the pool present at an address of the first array. The first and the second array can be used consecutively.

In other preferred embodiments, each address of the plurality further includes a second nucleic acid encoding a second amino acid sequence.

In one preferred embodiment, each address of the plurality includes a first test amino acid sequence that is common to all addresses of the plurality, and a second test amino acid sequence that is unique among all the addresses of the plurality. For example, the second test amino acid sequences can be query sequences whereas the first amino test amino acid sequence can be a target sequence. In another preferred embodiment, each address of the plurality includes a first test amino acid sequence that is unique among all the addresses of the plurality, and a second test amino acid sequence that is common to all addresses of the plurality. For example, the first test amino acid sequences can be query sequences whereas the second amino test amino acid sequence can be a target sequence. The second nucleic acid encoding the second test amino acid sequence can include a sequence encoding a recognition tag and/or an affinity tag.

At at least one address of the plurality, the first and second amino acid sequences can be such that they interact with one another. In one preferred embodiment, they are capable of binding to each other. The second test amino acid sequence is optionally fused to a detectable amino acid sequence, e.g., an epitope tag, an enzyme, a fluorescent protein (e.g., GFP, BFP, variants thereof). The second test amino acid sequence can be itself detectable (e.g., an antibody is available which specifically recognizes it). In another preferred embodiment, one is capable of modifying the other (e.g., making or breaking a bond, preferably a covalent bond, of the other). For example, the first amino acid sequence is kinase capable of phosphorylating the second amino acid sequence; the first is a methylase capable of methylating the second; the first is a ubiquitin ligase capable of ubiquitinating the second; the first is a protease capable of cleaving the second; and so forth.

Kits of these embodiments can be used to identify an interaction or to identify a compound that modulates, e.g., inhibits or enhances, an interaction.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

The kit can further include a database, e.g., in computer memory or a computer readable medium (e.g., a CD-ROM, a magnetic disc, flash memory. Each record of the database can include a field for the amino acid sequence encoded by the nucleic acid sequence and a descriptor or reference for the physical location of the nucleic acid sequence on the array. Optionally, the record also includes a field representing a result (e.g., a qualitative or quantitative result) of detecting the polypeptide encoded by the nucleic acid sequence. The database can include a record for each address of the plurality present on the array. The records can be clustered or have a reference to other records (e.g., including hierarchical groupings) based on the result.

The kit can also include instructions for use of the array or a link or indication of a network resource (e.g., a web site) having instructions for use of the array or the above database of records describing the addresses of the array.

In another aspect, the invention features a method of providing an array across a network, e.g., a computer network, or a telecommunications network. The method includes: providing a substrate comprising a plurality of addresses, each address of the plurality having a binding agent; providing a plurality of nucleic acid sequences, each nucleic acid sequence comprising a sequence encoding a test amino acid sequence and an affinity tag that is recognized by the binding agent; providing on a server a list of either (i) nucleic acid sequences of the plurality or (ii) subsets of the plurality (e.g., categorized groups of sequences); transmitting the list across a network to a user; receiving at least one selection of the list from the user; disposing the one or more nucleic acid sequence corresponding to the selection on an address of the plurality; and providing the substrate to the user.

In one embodiment, each nucleic acid sequence is disposed at a unique address. For example, if a subset is selected, each nucleic acid sequence of the subset is disposed at a unique address. In another embodiment, a plurality of nucleic acid sequences are disposed at each address.

The method can further include contacting each address of the plurality with one or more of (i) a transcription effector, and (ii) a translation effector. Optionally, the substrate is maintained under conditions permissive for the amino acid sequence to bind the binding agent. One or more addresses can then be washed, e.g., to remove at least one of (i) the nucleic acid, (ii) the transcription effector, (iii) the translation effector, and/or (iv) an unwanted polypeptide, e.g., an unbound polypeptide or unfolded polypeptide. The array can optionally be contacted with a compound, e.g., a chaperone; a protease; a protein-modifying enzyme; a small molecule, e.g., a small organic compound (e.g., of molecular weight less than 5000, 3000, 1000, 700, 500, or 300 Daltons); nucleic acids; or other complex macromolecules e.g., complex sugars, lipids, or matrix molecules.

The array can be further processed, e.g., prepared for storage. It can be enclosed in a package, e.g., an air- or water-resistant package. The array can be desiccated, frozen, or contacted with a storage agent (e.g., a cryoprotectant, an anti-bacterial, an anti-fungal). For example, an array can be rapidly frozen after being optionally contacted with a cryoprotectant. This step can be done at any point in the process (e.g., before or after contacting the array with an RNA polymerase; before or after contacting the array with a translation effector; or before or after washing the array). The packaged product can be supplied to a user with or without additional contents, e.g., a transcription effector, a translation effector, a vector nucleic acid, an antibody, and so forth.

In a preferred embodiment, each test amino acid sequence in the plurality of addresses is unique. For example, a test amino acid sequence can differ from all other test amino acid sequence of the plurality by 1, or more amino acid differences, (e.g., about 2, 3, 4, 5, 8, 16, 32, 64 or more differences; and, by way of example, has about 800, 256, 128, 64, or 32, 16, 8, 4, or fewer differences). In another preferred embodiment, the test amino acid sequence encoded by the nucleic acid at each address of the plurality is identical to all other test amino acid sequences in the plurality of addresses. In a preferred embodiment, the affinity tag encoded by the nucleic acid at each address of the plurality is the same, or substantially identical to all other affinity tags in the plurality of addresses. In another preferred embodiment, the nucleic acid at each address of the plurality encodes more than one affinity tag. In yet another preferred embodiment, the affinity tag encoded by the nucleic acid at an address of the plurality differs from at least one other affinity tag in the plurality of addresses.

In a preferred embodiment, the affinity tag is fused directly to the test amino acid sequence, e.g., directly amino-terminal, or directly carboxy-terminal. In another preferred embodiment, the affinity tag is separated from the test amino acid by one or more linker amino acids, e.g., 1, 2, 3, 4, 5, 6, 8, 10, 12, 20, 30 or more amino acids, preferably about 1 to 20, or about 3 to 12 amino acids. The linker amino acids can include a cleavage site, flexible amino acids (e.g., glycine, alanine, or serine, preferably glycine), and/or polar amino acids. The linker and affinity tag can be amino-terminal or carboxy-terminal to the test amino acid sequence.

The nucleic acid can be a RNA, or a DNA (e.g., a single-stranded DNA, or a double stranded DNA). In a preferred embodiment, the nucleic acid includes a plasmid DNA or a fragment thereof; an amplification product (e.g., a product generated by RCA, PCR, NASBA); or a synthetic DNA.

The nucleic acid can further include one or more of: a transcription promoter; a transcription regulatory sequence; a untranslated leader sequence; a sequence encoding a cleavage site; a recombination site; a 3' untranslated sequence; a transcriptional terminator; and an internal ribosome entry site. In one embodiment, the nucleic acid sequence includes a plurality of cistrons (also termed "open reading frames"), e.g., the sequence is dicistronic or polycistronic. In another embodiment, the nucleic acid also includes a sequence encoding a reporter protein, e.g., a protein whose abundance can be quantitated and can provide an indication of the quantity of test polypeptide fixed to the plate. The reporter protein can be attached to the test polypeptide, e.g., covalently attached, e.g., attached as a translational fusion. The reporter protein can be an enzyme, e.g., β-galactosidase, chloramphenicol acetyl transferase, β-glucuronidase, and so forth. The reporter protein can produce or modulate light, e.g., a fluorescent protein (e.g., green fluorescent protein, variants thereof, red fluorescent protein, variants thereof, and the like), and luciferase.

The transcription promoter can be a prokaryotic promoter, a eukaryotic promoter, or a viral promoter. In a preferred embodiment, the promoter is the T7 RNA polymerase promoter. The regulatory components, e.g., the transcription promoter, can vary among nucleic acids at different addresses of the plurality. For example, different promoters can be used to vary the amount of polypeptide produced at different addresses.

In one embodiment, the nucleic acid also includes at least one site for recombination, e.g., homologous recombination or site-specific recombination, e.g., a lambda att site or variant thereof; a lox site; or a FLP site. In a preferred embodiment, the recombination site lacks stop codons in the reading frame of a nucleic acid encoding a test amino acid sequence. In another preferred embodiment, the recombination site includes a stop codon in the reading frame of a nucleic acid encoding a test amino acid sequence.

In another embodiment, the nucleic acid includes a sequence encoding a cleavage site, e.g., a protease site, e.g., a site cleaved by a site-specific protease (e.g., a thrombin site, an enterokinase site, a PreScission site, a factor Xa site, or a TEV site), or a chemical cleavage site (e.g., a methionine, preferably a unique methionine (cleavage by cyanogen bromide) or a proline (cleavage by formic acid)).

The nucleic acid can include a sequence encoding a second polypeptide tag in addition to the affinity tag. The second tag can be C-terminal to the test amino acid sequence and the affinity tag can be N-terminal to the test amino acid sequence; the second tag can be N-terminal to the test amino acid sequence, and the affinity tag can be C-terminal to the test amino acid sequence; the second tag and the affinity tag can be adjacent to one another, or separated by a linker sequence, both being N-terminal or C-terminal to the test amino acid sequence. In one embodiment, the second tag is an additional affinity tag, e.g., the same or different from the first tag. In another embodiment, the second tag is a recognition tag. For example, the recognition tag can report the presence and/or amount of test polypeptide at an address. Preferably the recognition tag has a sequence other than the sequence of the affinity tag. In still another embodiment, a plurality of polypeptide tags (e.g., less than 3, 4, 5, about 10, or about 20 tags) are encoded in addition to the first affinity tag. Each polypeptide tag of the plurality can be the same as or different from the first affinity tag.

The nucleic acid sequence can further include an identifier sequence, e.g., a non-coding nucleic acid sequence, e.g., one that is synthetically inserted, and allows for uniquely identifying the nucleic acid sequence. The identifier sequence can be sufficient in length to uniquely identify each sequence in the plurality; e.g., it is about 5 to 500, 10 to 100, 10 to 50, or about 10 to 30 nucleotides in length. The identifier can be selected so that it is not complementary or identical to another identifier or any region of each nucleic acid sequence of the plurality on the array.

The test amino acid sequence can further include a protein splicing sequence or intein. The intein can be inserted in the middle of a test amino acid sequence. The intein can be a naturally-occurring intein or a mutated intein.

The nucleic acid sequences of the plurality can be obtained from a collection of full-length expressed genes (e.g., a repository of clones), a cDNA library, or a genomic library. The test amino acid sequences can be genes expressed in a tissue, e.g., a normal or diseased tissue. The test polypeptides can be mutants or variants of a scaffold protein (e.g., an antibody, zinc-finger, polypeptide hormone etc.). In yet another embodiment, the test polypeptides are random amino acid sequences, patterned amino acids sequences, or designed amino acids sequences (e.g., sequence designed by manual, rational, or computer-aided approaches). The plurality of test amino acid sequences can include a plurality from a first source, and plurality from a second source. For example, the server can be provided with lists of test amino acid sequences associated with a diseased tissue or a first species in addition to lists of test amino acid sequences associated with a normal tissue or a second species.

The binding agent can be attached to the substrate. For example, the substrate can be derivatized and the binding agent covalent attached thereto. The binding agent can be attached via a bridging moiety, e.g., a specific binding pair. (e.g., the substrate contains a first member of a specific binding pair, and the binding agent is linked to the second member of the binding pair, the second member being attached to the substrate).

In yet another embodiment, an insoluble substrate (e.g., a bead or particle), is disposed at each address of the plurality, and the binding agent is attached to the insoluble substrate. The insoluble substrate can further contain information encoding its identity, e.g., a reference to the address on which it is disposed. The insoluble substrate can be tagged using a chemical tag, or an electronic tag (e.g., a transponder). The insoluble substrate can be disposed such that it can be removed for later analysis.

The invention also features a computer system including (i) a server storing a list of amino acid sequences and/or their descriptors, and (ii) software configured to: (1) send a list of amino acid sequence and/or their descriptors to a client; (2) receive from the client a plurality of selected amino acid sequences from the list; and (3) interface with an array provider (e.g., a robotic system, or a technician) so as to dispose on a substrate nucleic acids encoding the selected amino acid sequences, each at a plurality of addresses.

The invention also features a method of identifying a small molecule or drug binding protein. Such proteins can include drug targets and adventitious drug-binding proteins (e.g., non-target proteins responsible for toxicity of a drug). The method includes providing or obtaining an array described herein, contacting each address of the plurality with a drug, e.g., a labeled drug. The method can further include detecting the presence of the drug at each address of the plurality. The method can also include a wash step, e.g., prior to the detecting.

The term "array," as used herein, refers to an apparatus with a plurality of addresses.

A "nucleic acid programmable polypeptide array" or "NAPPA" refers to an array described herein. The term encompasses such an array at any stages of production, e.g., before any nucleic acid or polypeptide is present; when nucleic acid is disposed on the array, but no polypeptide is present; when a nucleic acid has been removed and a polypeptide is present; and so forth.

The term "address," as referred to herein, is a positionally distinct portion of a substrate. Thus, a reagent at a first address can be positionally distinguished from a reagent at a second address. The address is located in and/or on the substrate. The address can be distinguished by two coordinates (e.g., x-y) in embodiments using two-dimensional arrays, or by three coordinates (e.g., x-y-z) in embodiments using three-dimensional arrays.

The term "substrate," as used herein in the context of arrays (as opposed to a substrate of an enzyme), refers to a composition in or on which a nucleic acid or polypeptide is disposed. The substrate may be discontinuous. An illustrative case of a discontinuous substrate is a set of gel pads separated by a partition.

The terms "test amino acid sequence" or "test polypeptide," as used herein, refers to a polypeptide of at least three amino acids that is translated on the array. The test amino acid sequence may or may not vary among the addresses of the array.

The term "translation effector" refers to a macromolecule capable of decoding a messenger RNA and forming peptide bonds between amino acids. The term encompasses ribosomes, and catalytic RNAs with the aforementioned property. A translation effector can optionally further include tRNAs, tRNA synthases, elongation factors, initiation factors, and termination factors. An example of a translation effector is a translation extract obtained from a cell.

As used herein, the term "transcription effector" refers to a composition capable of synthesizing RNA from an RNA or DNA template, e.g., a RNA polymerase.

The term "recognizes," as used herein, refers to the ability of a first agent to bind to a second agent. Preferably, the dissociation constant or apparent dissociation constant of binding is about 100 $\mu$M, 10 $\mu$M, 1 $\mu$M, 100 nM, 10 nM, 1 nM, 100 pM, 10 pM, or less.

The term "affinity tag," as used herein, refers to an amino acid, a peptide sequence, or a polypeptide sequence that includes a moiety capable of recognizing or reacting with a binding agent.

The term "binding agent," as used herein, refers to a moiety, either a biological polymer (e.g., polypeptide, polysaccharide, or nucleic acid, or another chemical compound which is capable of recognizing or binding an affinity tag or which is capable of specifically reacting with an affinity tag, e.g., to form a covalent bond. The term "handle" is used synonymously with binding agent.

The term "recognition tag," as used herein, refers to an amino acid, a peptide sequence, or a polypeptide sequence that can be detected, directly or indirectly, on the array.

As used herein, the terms "peptide," "polypeptide," and "protein" are used interchangeably. Generally, these terms refer to polymers of amino acids which are at least three amino acids in length.

A "unique reagent" refers to a reagent that differs from a reagent at each other address in a plurality of addresses. The reagent can differ from the reagents at other addresses in terms of one or both of: structure and function. A unique reagent can be a molecule, e.g., a biological macromolecule (e.g., a nucleic acid, a polypeptide, or a carbohydrate), a cell, or a small organic compound. In the case of biological polymers, a structural difference can be a difference in sequence at at least one position. In addition, a structural difference, e.g., for polymers having the same sequence, can be a difference in conformation (e.g., due to allosteric modification; meta-stable folding; alternative native folded states; prion or prion-like properties) or a modification (e.g., covalent and non-covalent modifications (e.g., a bound ligand)).

Protein microarrays representing many different proteins, as described herein, provide a potent high-throughput tool which can greatly accelerate the study of protein function. The arrays described herein avoids the process of expressing proteins in living cells, purifying, stabilizing, and spotting them. NAPPA arrays, as described herein, also reduce the number of manipulations for each polypeptide, as the polypeptide can be synthesized in situ in or on the array substrate. The current invention obviates the need to purify polypeptides and to manipulate purified protein samples onto the array by the straightforward and much simpler process of disposing nucleic acids. The nucleic acids are then simultaneously transcribed/translated in a cell-free system and immobilized in situ, minimizing direct manipulation of the proteins and making this approach well suited to high-throughput applications. Further, the cotranslation of a first and second polypeptide can enhance complex formation in some cases.

In addition, the protein folding environment in cell free systems differs from the natural environment, allowing for a user to control a variety of parameters such as post-translational modifications.

The array can be easily reprogrammed to contain different sets of proteins and polypeptides.

Polypeptide arrays provide comprehensive genome-wide screens for biomolecular interactions. The arrays, as described herein, allow for the sampling of an entire library. Detecting each address of a plurality provides the certainty that each library member has been screened. Thus, complete coverage of known sequences is possible. For example, a single array containing 10,000 arrayed elements, for example, can be sufficient to yield 10,000 results (e.g., quantitative results), each result comparable with the results of other elements of the array, and potentially with a result from other arrays. High-density arrays further expand possible coverage.

Some embodiments described herein also provide arrays and methods for detecting subtle and sensitive results. As a polypeptide species, e.g., a homogenous species, can be provided at an address without competing species, a result for the individual species can be detected. In other embodiments, arrays and methods can also including competing species for the very purpose of removing subtle results and increasing the signal of strong positives.

In sum, the arrays and methods described herein provide a versatile new platform for proteomics.

DETAILED DESCRIPTION

Figure 1:
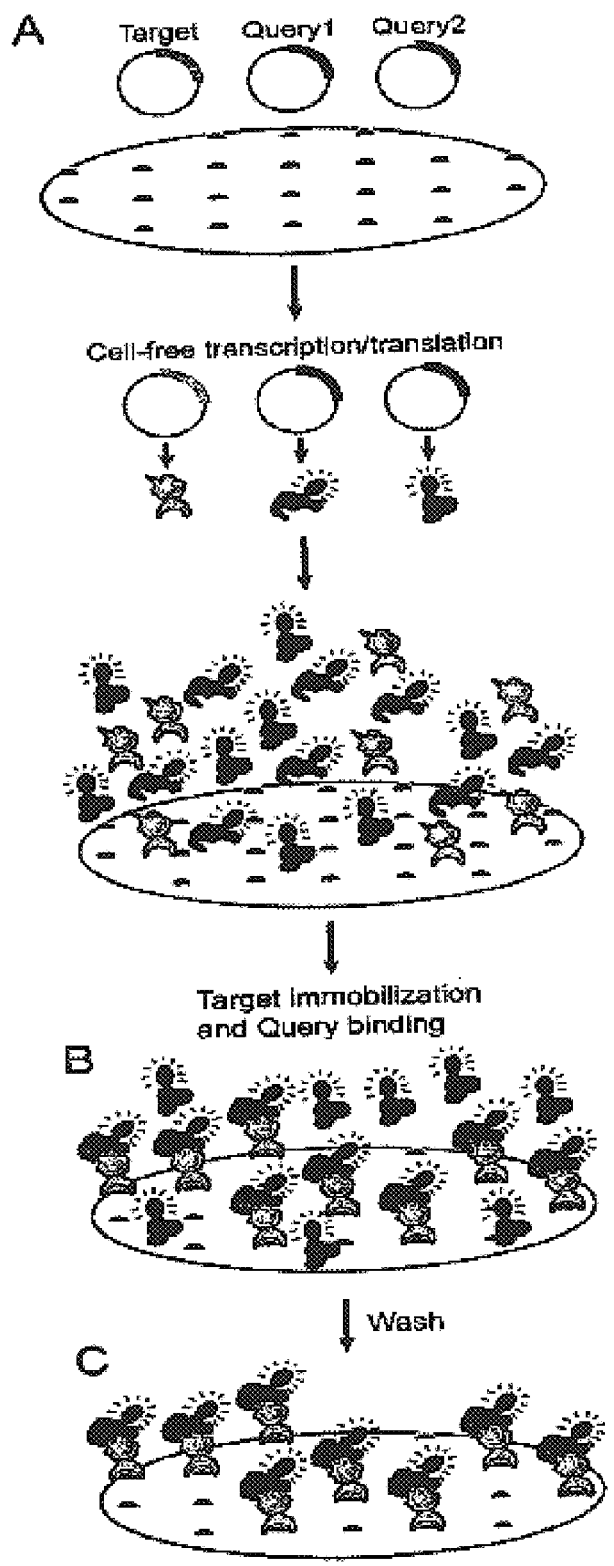
FIG. 1 is a schematic representation of use of a nucleic acid programmable array (NAPPA) for screening protein-protein interactions. (A) Plasmids encoding target proteins fused with an affinity tag such as GST and query proteins fused with a reporter tag such as GFP are deposited in wells derivatized with affinity acceptor molecules such as glutathione. The fusion proteins are transcribed/translated in a cell-free expression system. (B) Target proteins are immobilized in the wells, as are query proteins that bind to target. The wells are then washed to remove unbound protein. (C) Target-query complexes are detected by fluorescence spectroscopy.

All patents and references cited herein are incorporated in their entirety by reference.

Substrates

Materials.

Both solid and porous substrates are suitable for recipients for the encoding nucleic acids described herein. A substrate material can be selected and/or optimized to be compatible with the spot size (e.g., density) required and the application.

In one embodiment, the substrate is a solid substrate. Potentially useful solid substrates include: mass spectroscopy plates (e.g., for MALDI), glass (e.g., functionalized glass, a glass slide, porous silicate glass, a single crystal silicon, quartz, UV-transparent quartz glass), plastics and polymers (e.g., polystyrene, polypropylene, polyvinylidene difluoride, poly-tetrafluoroethylene, polycarbonate, PDMS, acrylic), metal coated substrates (e.g., gold), silicon substrates, latex, membranes (e.g., nitrocellulose, nylon), a glass slide suitable for surface plasmon resonance (SPR).

In another embodiment, the substrate is porous, e.g., a gel or matrix. Potentially useful porous substrates include: agarose gels, acrylamide gels, sintered glass, dextran, meshed polymers (e.g., macroporous crosslinked dextran, sephacryl, and sepharose), and so forth.

Substrate Properties.

The substrate can be opaque, translucent, or transparent. The addresses can be distributed, on the substrate in one dimension, e.g., a linear array; in two dimensions, e.g., a planar array; or in three dimensions, e.g., a three dimensional array. The solid substrate may be of any convenient shape or form, e.g., square, rectangular, ovoid, or circular. In another embodiment, the solid substrate can be disc shaped and attached to a means of rotation.

In one embodiment, the substrate contains at least 1, 10, 100, $10^3$, $10^4$, $10^5$, $10^6$, $10^7$, $10^8$, or $10^9$ or more addresses per cm$^2$. The center to center distance can be 5 mm, 1 mm, 100 μm, 10 μm, 1 μm, 100 nm or less. The longest diameter of each address can be 5 mm, 1 mm, 100 μm, 10 μm, 1 μm, 100 nm or less. In one embodiment, each addresses contains 0 μg, 1 μg, 100 ng, 10 ng, 1 ng, 100 pg, 10 pg, 1 pg, 0.1 pg, or less of the nucleic acid. In another embodiment, each address contains 100, $10^3$, $10^4$, $10^5$, $10^6$, $10^7$, $10^8$, or $10^9$ or more molecules of the nucleic acid.

Substrate Modification.

The substrate can be modified to facilitate the stable attachment of linkers, capture probes, or binding agents. Generally, a skilled artisan can use routine methods to modify a substrate in accordance with the desired application. The following are non-limiting examples of substrate modifications.

A surface can be amidated, e.g., by silylating the substrate, e.g., with trialkoxyaminosilane. Silane-treated surface can also be derivatized with homobifunctional and heterobifunctional linkers. The substrate can be derivatized, e.g., so it has a hydroxy, an amino (e.g., alkylamine), carboxyl group, N-hydroxy-succinimidyl ester, photoactivatable group, sulfhydryl, ketone, or other functional group available for reaction. The substrates can be derivatized with a mask in order to only derivatized limited areas; a chemical etch or UV light can be used to remove derivatization from selected regions.

Thus, for the preparation of glass slides, options are to derivatize the individual spots, or to derivatize the entire slide then use a physical mask, chemical etch, or UV light to cover or remove the derivatization in the areas between spots.

Partitioned Substrates.

In one preferred embodiment, each address is partitioned from all other addresses in order to prevent unique molecules from diffusing to other addresses. The following are possible marcomolecules which must remain localized at the address: a template nucleic acid encoding the test amino acid sequence; amplified nucleic acid encoding the test amino acid sequence; mRNA encoding the test amino acid sequence; ribosomes, e.g., monosomes and polysomes, translating the mRNA; and the translated polypeptide.

The substrate can be partitioned, e.g., depressions, grooves, photoresist. For example, the substrate can be a microchip with microchannels and reservoirs etched therein, e.g., by photolithography. Other non-limiting examples of substrates include multi-welled plates, e.g., 96-, 384-, 1536-, 6144-well plates, and PDMS plates. Such high-density plates are commercially available, often with specific surface treatments. Depending on the optimal volume required for each application, an appropriate density plate is selected. In another embodiment, the partitions are generated by a hydrophobic substance, e.g., a Teflon mask, grease, or a marking pen (e.g., Snowman, Japan).

In one embodiment, the substrate is designed with reservoirs isolated by protected regions, e.g., a layer of photoresist. For example, for each address, a translation effector can be isolated in one reservoir, and the nucleic acid encoding a test amino acids sequence can be isolated in another reservoir. A mask can be focused or placed on the substrate, and a photoresist barrier separating the two reservoirs can be removed by illumination. The translation effector and the nucleic acid reservoirs are mixed. The method can also include moving the substrate in order to facilitate mixing. After sufficient incubation for translation to occur, and for the nascent polypeptides to bind to a binding agent, e.g., an agent attached to the substrate, additional photoresist barriers can be removed with a second mask to facilitate washing a subset or all the addresses of the substrate, or applying a second compound to each address.

Planar Substrates.

In another embodiment, the addresses are not physically partitioned, but diffusion is limited on the planar substrate, e.g., by increasing the viscosity of the solution, by providing a matrix with small pore size which excludes large macromolecules, and/or by tethering at least one of the aforementioned macromolecules. Preferably, the addresses are sufficiently separated that diffusion during the time required for translation does not result in excessive displacement of the translated polypeptide to an address other than its original address on the array. In yet another embodiment, modest or even substantial diffusion to neighboring addresses is permitted. Results, e.g., a signal of a label, are processed, e.g., using a computer system, in order to determine the position of the center of the signal. Thus, by compensating for radial diffusion, the unique address of the translated polypeptide can be accurately determined.

Three-Dimensional Substrates.

A three-dimensional substrate can be generated, e.g., by successively applying layers of a gel matrix on a substrate. Each layer contains a plurality of addresses. The porosity of the layers can vary, e.g., so that alternating layers have reduced porosity.

In another embodiment, a three-dimensional substrate includes stacked two-dimensional substrates, e.g., in a tower format. Each two-dimensional substrate is accessible to a dispenser and detector.

Micromachined Chips.

Chips are made with glass and plastic materials, using rectangular or circular geometry. Wells and fluid channels are machined into the chip, and then the surfaces are derivatized. Plasmids solutions would be spotted on the chip and allowed to dry, and then a cover would be applied. Cell-free transcription/translation mix would be added via the micromachined channels. The cover prevents evaporation during incubation. A humidity-controlled chamber can be used to prevent evaporation.

CD Format.

A disk geometry (also termed "CD format") is another suitable substrate for the microarray. Sample addition and reactions are performed while the disk is spinning (see PCT WO 00/40750; WO 97/21090; GB patent application 9809943.5; "The next small thing" (Dec. 9, 2000) *Economist Technology Quarterly* p. 8; PCT WO 91/16966; Duffy et al. (1999) *Analytical Chemistry;* 71, 20, (1999), 4669–4678). Thus, centrifugal force drives the flow of transcription/translation mix and wash solutions.

The disc can include sample-loading areas, reagent-loading areas, reaction chambers, and detection chambers. Such microfluidic structures are arranged radially on the disc with the originating chambers located towards the disc center. Samples from a microtiter plate can be loaded using a liquid train and a piezo dispenser. Multiple samples can be separated in the liquid train by air gaps or an inert solution. The piezo dispenser then dispenses each sample onto appropriate application areas on the CD surface, e.g., a rotating CD surface. The volume dispensed can vary, e.g., less than about 10 pL, 50 pL, 100 pL, 500 pL, 1 nL, 5 nL, or 50 nL. After entry on the CD, the centripetal force conveys the dispensed nucleic acid sample into appropriate reaction chambers. Flow between chambers can be guided by barriers, transport channels, and/or surface interactions (e.g., between the walls and the solution). The depth of channels and chambers can be adjusted to control volume and flow rate in each area.

A master CD can be made by deep reactive ion etching (DRIE) on a 6-inch silicon wafer. This master disc can be plated and used as a model to manufacture additional CDs by injection molding (e.g., Amic AB, Uppsala, Sweden).

A stroboscopic can be used to synchronize the detector with the rotation of the CD in order to track individual detection chambers.

Transcription Effectors

RNA-directed RNA polymerases and DNA-directed RNA polymerases are both suitable transcription effectors.

DNA-directed RNA polymerases include bacteriophage T7 polymerase, phage T3, phage φII, Salmonella phage SP6, or Pseudomonas phage gh-1, as well as archeal RNA polymerases, bacterial RNA polymerase complexes, and eukaryotic RNA polymerase complexes.

T7 polymerase is a preferred polymerase. It recognizes a specific sequence, the T7 promoter (see e.g., U.S. Pat. No. 4,952,496), which can be appropriately positioned upstream of an encoding nucleic acid sequence. Although, a DNA duplex is required for recruitment and initiation of T7 polymerase, the remainder of the template can be single stranded. In embodiments utilizing other RNA polymerases, appropriate promoters and initiations sites are selected according to the specificity of the polymerase.

RNA-directed RNA polymerases can include Qβ replicase, and RNA-dependent RNA polymerase.

Translation Effectors

In one embodiment, the transcription/translation mix is in a minimal volume, and this volume is optimized for each application. The volume of translation effector at each address can be less than about $10^{-4}$, $10^{-5}$, $10^{-6}$, $10^{-7}$, $10^{-8}$, or $10^{-9}$ L. During dispensing and incubation, the array can be maintained in an environment to prevent evaporation, e.g., by covering the wells or by maintaining a humid atmosphere.

In another embodiment, the entire substrate can be coated or immersed in the translation effector. One possible translation effector is a translation extract prepared from cells. The translation extract can be prepared e.g., from a variety of cells, e.g., yeast, bacteria, mammalian cells (e.g., rabbit reticulocytes), plant cells (e.g., wheat germ), and archebacteria. In a preferred embodiment, the translation extract is a wheat germ agglutinin extract or a rabbit reticulocyte lysate. In another preferred embodiment, the translation extract also includes a transcription system, e.g., a eukaryotic, prokaryotic, or viral RNA polymerase, e.g., T7 RNA polymerase. In a preferred embodiment, the translation extract is disposed on the substrate such that it can be removed by simple washing. The translation extract can be supplemented, e.g., with additional amino acids, tRNAs, tRNA synthases, and energy regenerating systems. In one embodiment, the translation extract also include an amber, ochre, or opal suppressing tRNA. The tRNA can be modified to contain an unnatural amino acid. In another embodiment, the translation extract further includes a chaperone, e.g., an agent which unfolds or folds polypeptides, (e.g., a recombinant purified chaperones, e.g., heat shock factors, GroEL/ES and related chaperones, and so forth. In another embodiment, the translation extract includes additives (e.g., glycerol, polymers, etc.) to alter the viscosity of the extract.

Affinity Tags

An amino acid sequence that encodes a member of a specific binding pair can be used as an affinity tag. The other member of the specific binding pair is attached to the substrate, either directly or indirectly.

One class of specific binding pair is a peptide epitope and the monoclonal antibody specific for it. Any epitope to which a specific antibody is or can be made available can serve as an affinity tag. See Kolodziej and Young (1991) *Methods Enz.* 194:508–519 for general methods of providing an epitope tag. Exemplary epitope tags include HA (influenza haemagglutinin; Wilson et al. (1984) *Cell* 37:767), myc (e.g., Myc1-9E10, Evan et al. (1985) *Mol. Cell. Biol.* 5:3610–3616), VSV-G, FLAG, and 6-histidine (see, e.g., German Patent No. DE 19507 166).

An antibody can be coupled to a substrate of an array, e.g., indirectly using *Staphylococcus aereus* protein A, or streptococcal protein G. The antibody can be covalently bound to a derivatized substrate, e.g., using a crosslinker, e.g., N-hydroxy-siccinimidyl ester. The test polypeptides with epitopes such as Flag, HA, or myc are bound to antibody-coated plates.

Another class of specific binding pair is a small organic molecule, and a polypeptide sequence that specifically binds it. See, for example, the specific binding pairs listed in Table 1.

TABLE 1

| Protein | Ligand |
| --- | --- |
| glutathione-S-transferase, | glutathione |
| chitin binding protein | chitin |
| Cellulase (CBD) | cellulose |
| maltose binding protein | amylose, or maltose |
| dihydrofolate reductases | methotrexate |
| FKBP | FK506 |

Additional art-known methods of tethering proteins, e.g., the use of specific binding pairs are suitable for the affinity or chemical capture of polypeptides on the array. Appropriate substrates include commercially available streptavidin and avidin-coated plates, for example, 96-well Pierce Reacti-Bind Metal Chelate Plates or Reacti-Bind Glutathione Coated Plates (Pierce, Rockford, Ill.). Histidine- or GST-tagged test polypeptides are immobilized on either 96-well Pierce Reacti-Bind Metal Chelate Plates or Reacti-Bind Glutathione Coated Plates, respectively, and unbound proteins are optionally washed away.

In one embodiment, the polypeptide is an enzyme, e.g., an inactive enzyme, and ligand is its substrate. Optionally, the enzyme is modified so as to form a covalent bond with its substrate. In another embodiment, the polypeptide is an enzyme, and the ligand is an enzyme inhibitor.

Yet another class of specific binding pair is a metal, and a polypeptide sequence which can chelate the metal. An exemplary pair is $Ni^{2+}$ and the hexa-histidine sequence (see U.S. Pat. Nos. 4,877,830; 5,047,513; 5,284,933; and 5,130,663.).

In still another embodiment, the affinity tag is a dimerization sequence, e.g., a homodimerization or heterodimerization sequence., preferably a heterodimerization sequence. In one illustrative example, the affinity tag is a coiled-coil sequence, e.g., the heptad repeat region of Fos. The binding agent coupled to the array is the heptad repeat region of Jun. The test polypeptide is tethered to the substrate by heterodimization of the Fos and Jun heptad repeat regions to form a coiled-coil.

In another embodiment (see also unnatural amino acids), the affinity tag is provided by an unnatural amino acid, e.g., with a side chain having functional properties different from a naturally occurring amino acid. The binding agent attached to the substrate functions as a chemical handle to either bind or react with the affinity tag.

In a related embodiment, the affinity tag is a free cysteine which can be oxidized with a thiol group attached to the substrate to create a disulfide bond that tethers the test polypeptide.

Disposal of Nucleic Acid Sequences on Arrays

The substrate and the liquid-handling equipment are selected with consideration for required liquid volume, positional accuracy, evaporation, and cross-contamination. The density of spots can depend on the liquid volume required for a particular application, and on the substrate, e.g., how much a liquid drop spreads on the substrate due to surface tension, and the positional accuracy of the dispensing equipment.

Numerous methods are available for dispensing small volumes of liquid onto substrates. For example, U.S. Pat. No. 6,112,605 describes a device for dispensing small volumes of liquid. U.S. Pat. No. 6,110,426 describes a capillary action-based method of dispensing known volumes of a sample onto an array.

Nucleic acid spotted onto slides can be allowed to dry by evaporation. Dry air can be used to accelerate the process.

Capture Probes.

The substrate can include an attached nucleic acid capture probe at each address. In one aspect, capture probes can be used create a self-assembling array. A unique capture probe at each address selectively hybridizes to a nucleic acid encoding a test amino acid sequence, thereby organizing each encoding nucleic acid to a unique address. The capture nucleic acid can be covalently attached or bound, e.g., to a polycationic surface on the substrate.

The capture probe can itself be synthesized in situ, e.g., by a light-directed method (see, e.g., U.S. Pat. No. 5,445,934), or by being spotted or disposed at the addresses. The capture probe can hybridize to the nucleic acid encoding the test polypeptide. In a preferred embodiment, the capture probe anneals to the T7 promoter region of a single stranded nucleic acid encoding the test amino acid sequence. In another embodiment, the capture probe is ligated to the encoding nucleic acid sequence. In yet another embodiment, the capture probe is a padlock probe. In still another embodiment, the capture probe hybridizes to a nucleic acid encoding a test amino acid sequence, e.g., a unique region of the nucleic acid, or to a nucleic acid sequence tag provided on the nucleic acid for the purposes of identification.

Disposed Insoluble Substrates

One or more insoluble substrates having a binding agent attached can be disposed at each address of the array. The insoluble substrates can further include a unique identifier, such as a chemical, nucleic acid, or electronic tag. Chemical tags, e.g., such as those used for recursive identification in "split and pool" combinatorial syntheses. Kerr et al. (1993) *J. Am. Chem. Soc.,* 115:2529–253 1) Nikolaiev et al. ((1993) *Peptide Res.* 6, 161–170) and Ohlmeyer et al. ((11993) *Proc. Natl. Acad. Sci. USA* 90:10922–10926) describe methods for coding and decoding such tags. A nucleic acid tag can be a short oligonucleotide sequence that is unique for a given address. The nucleic acid tag can be coupled to the particle. In another embodiment, the encoding nucleic acid provides a unique identifier. The encoding nucleic acid can be coupled or attached to the particle. Electronic tags include transponders as mentioned below. The insoluble substrate can be a particle (e.g., a nanoparticle, or a transponder), or a bead.

Beads.

The disposed particle can be a bead, e.g., constructed from latex, polystyrene, agarose, a dextran (sepharose, sephacryl), and so forth.

Transponders.

U.S. Pat. No. 5,736,332 describes methods of using small particles containing a transponder on which a handle or binding agent can be affixed. The identity of the particle is discerned by a read-write scanner device which can encode and decode data, e.g., an electronic identifier, on the particle (see also Nicolaou et al. (1995) *Angew. Chem. Int. Ed. Engl.* 34:2289–2291). Test polypeptides are bound to the transponder by attaching to the handle or binding agent.

Disposed Nucleic Acid Sequences

Any appropriate nucleic acid for translation can be disposed at an address of the array. The nucleic acid can be an RNA, single stranded DNA, a double stranded DNA, or combinations thereof. For example, a single-stranded DNA can include a hairpin loop at its 5' end which anneals to the T7 promoter sequence to form a duplex in that region. The nucleic acid can be an amplification products, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166).

In one embodiment, the sequence of the encoding nucleic acid is known prior to being disposed at an address. In another embodiment, the sequence of the encoding nucleic acid is unknown prior to disposal at an address. For example, the nucleic acid can be randomly obtained from a library. The nucleic acid can be sequenced after the address on which it is placed has been identified as encoding a polypeptide of interest.

Amplification in situ

A nucleic acid disposed on the array can be amplified directly on the array, by a variety of methods, e.g., PCR (U.S. Pat. Nos. 4,683,196 and 4,683,202); rolling circle amplification ("RCA," U.S. Pat. No. 5,714,320), isothermal RNA amplification or NASBA, and strand displacement amplification (U.S. Pat. No. 5,455,166).

Isothermal RNA amplification or "NASBA" is well described in the art (see, e.g., U.S. Pat. Nos. 5,130,238; 5,409,818; and 5,554,517; Romano et al. (1997) *Immunol Invest.* 26:15–28; in technical literature for "RnampliFire™" Qiagen, Calif.). Isothermal RNA amplification is particularly suitable as reactions are homogenous, can be performed at ambient temperatures, and produce RNA templates suitable for translation.

Vectors for Expression

Coding regions of interest can be taken from a source plasmid, e.g., containing a full length gene and convenient restriction sites, or sites for homologous or site-specific recombination, and transferred to an expression vector. The expression vector includes a promoter and an operably linked coding region, e.g., encoding an affinity tag, such as one described herein. The tag can be N or C terminal. The vector can carry a cap-independent translation enhancer (CITE, or IRES, internal ribosome entry site) for increased in vitro translation of RNA prepared from cloned DNA sequences. The fusion proteins will be generated with commercially available in vitro transcription/translation kits such as the Promega TNT Coupled Reticulocyte Lysate Systems or TNT Coupled Wheat Germ Extract Systems. Cell-free extracts containing translation component derived from microorganisms, such as a yeast, or a bacteria, can also be used.

In addition, the vector can include a number of regulatory sequences such as a transcription promoter; a transcription regulatory sequence; a untranslated leader sequence; a sequence encoding a protease site; a recombination site; a 3' untranslated sequence; a transcriptional terminator; and an internal ribosome entry site.

The vector or encoding nucleic acid can also include a sequence encoding an intein. Methods of using inteins for the regulated removal of an intervening sequence are described, e.g., in U.S. Pat. Nos. 5,496,714 and 5,834,247. Inteins can be used to cyclize, ligate, and/or polymerize polypeptides, e.g., as described in Evans et al. (1999) *J. Biol Chem* 274:3923 and Evans et al. (1999) *J Biol Chem* 274:18359.

Exemplary Useful Sequences

Naturally Occurring Sequences.

Useful encoding nucleic acid sequence for creating arrays include naturally occurring sequences. Such nucleic acids can be stored in a repository, see below. Nucleic acid sequences can be procured from cells of species from the kingdoms of animals, bacteria, archebacteria, plants, and fungi. Non-limiting examples of eukaryotic species include: mammals such as human, mouse (*Mus musculus*), and rat; insects such as *Drosophila melanogaster*; nematodes such as *Caenorhabditis elegans*; other vertebrates such as *Brachydanio rerio*; parasites such as *Plasmodium falciparum,*

*Leishmania major*; fungi such as yeasts, Histoplasma, Cryptococcus, *Saccharomyces cerevisiae, Schizosaccharomyces pombe, Pichia pastoris* and the like); and plants such as *Arabidoposis thaliana*, rice, maize, wheat, tobacco, tomato, potato, and flax. Non-limiting examples of bacterial species include *E. coli, B. subtilis, Mycobacterium tuberculosis, Pseudomonas aeriginosa, Vibrio cholerae, Thernatoga maritime, Mycoplasma pneumoniae, Mycoplasma genitalium, Helicobacter pylori, Neisseria meningitidis*, and *Borrelia burgdorferi*. In additional, amino acid sequence encoded by viral genomes can be used, e.g., a sequence from rotavirus, hepatitis A virus, hepatitis B virus, hepatitis C virus, herpes virus, papilloma virus, or a retrovirus (e.g., HIV-1, HIV-2, HTLV, SIV, and STLV).

In a preferred embodiment, a cDNA library is prepared from a desired tissue of a desired species in a vector described herein. Colonies from the library are picked, e.g., using a robotic colony picker. DNA is prepared from each colony and used to program a NAPPA array.

Artificial Sequences.

The encoding nucleic acid sequence can encode artificial amino acid sequences. Artificial sequences can be randomized amino acid sequences, patterned amino acid sequence, computer-designed amino acid sequences, and combinations of the above with each other or with naturally occurring sequences. Cho et al. (2000) *J Mol Biol* 297:309–19 describes methods for preparing libraries of randomized and patterned amino acid sequences. Similar techniques using randomized oligonucleotides can be used to construct libraries of random sequences. Individual sequences in the library (or pools thereof) can be used to program a NAPPA array.

Dahiyat and Mayo (1997) *Science* 278:82–7 describe an artificial sequence designed by a computer system using the dead-end elimination theorem. Similar systems can be used to design amino acid sequences, e.g., based on a desired structure, such that they fold stably. In addition, computer systems can be used to modify naturally occurring sequences in order Mutagenesis.

The array can be used to display the products of a mutagenesis or selection. Examples of mutagenesis procedures include cassette mutagenesis (see e.g., Reidhaar-Olson and Sauer (1988) *Science* 241:53–7), PCR mutagenesis (e.g., using manganese to decrease polymerase fidelity), in vivo mutagenesis (e.g., by transfer of the nucleic acid in a repair deficient host cell), and DNA shuffling (see U.S. Pat. Nos. 5,605,793; 5,830,721; and 6,132,970). Examples of selection procedures include complementation screens, and phage display screens In addition, more methodical variation can be achieved. For example, an amino acid position or positions of a naturally occurring protein can be systematically varied, such that each possible substitution is present at a unique position on the array. For example, the all the residues of a binding interface can be varied to all possible other combinations. Alternatively, the range of variation can be restricted to reasonable or limited amino acid sets.

Collections.

Additional collections include arrays having at different addresses one of the following combinations: combinatorial variants of a bioactive peptide; specific variants of a single polypeptide species (splice variants, isolated domains, domain deletions, point mutants); polypeptide orthologs from different species; polypeptide components of a cellular pathway (e.g., a signalling pathway, a regulatory pathway, or a metabolic pathway); and the entire polypeptide complement of an organism.

Repositories of Nucleic Acids

The arrays described herein can be produced from nucleic acid sequences in a large repository. For example, commercial and academic institutions are providing large-scale repositories of all known and/or available genes and predicted open reading frames (ORFs) from human and other commonly studied organism, both eukaryotic, prokaryotic, and archeal. For example, the collection can contain 500, 1,000, 10,000, 20,000, 30,000 50,000, 100,000 or more full-length sequences. One example of such a repository is the FLEX (Full Length EXpression) Repository (Harvard Institute of Proteomics, Harvard Medical School, Boston, Mass.). The repository can be maintained as a clone bank, e.g., of frozen bacteria transformed with a plasmid containing a full-length coding region. A central computing unit can control access and information regarding each full-length coding region. For example, each clone can be accessible to a robot and can be tracked and verified, e.g., by a locator (e.g., a bar code, a transponder, or other electronic identifier). Thus, a desired construct can be obtained from the repository through a network-based user interface without manual intervention. The computing unit can also collate and maintain any information gathered by experimentation or by other databases regarding each clone. For example, each sample can be linked to a network-accessible relational database that tracks its bioinformatics data, storage location and cloning history, as well as any relevant links to other biological databases.

The clones in the collection can be maintained and produced in a format compatible with a recombinational cloning system that enables automated directional and in-frame shuttling of genes into virtually any expression or functional vector, obviating the need for standard subcloning approaches. The conventional production of various expression constructs requires a slow process of subcloning using restriction enzymes and ligases. Because of the variability in available restriction sites, each gene requires an individualized cloning strategy that may need to be altered for every different expression assay depending on the available sites in the necessary plasmids. In contrast, recombinational cloning, described below, is a novel alternative technique that is highly efficient, rapid, and easily scaled for high-throughput performance.

Recombinational Cloning

Methods for recombinational cloning are well known in the art (see e.g., U.S. Pat. No. 5,888,732; Walhout et al. (2000) Science 287:116; Liu et al. (1998) *Curr. Biol.* 8(24): 1300–9.). Recombinational cloning exploits the activity of certain enzymes that cleave DNA at specific sequences and then rejoin the ends with other matching sequences during a single concerted reaction.

U.S. Pat. No. 5,888,732 describes a system based upon the site-specific recombination of bacteriophage lambda and uses double recombination. In double recombination, any DNA fragment that resides between the two different recombination sites will be transferred to a second vector that has the corresponding complementary sites. The system relies on two vectors, a master clone vector and a target vector. The one harboring the original gene is known as the master clone. The second plasmid is the target vector, the vector required for a specific application, such as a vector described herein for programming an array. Different versions of the expression vectors are designed for different applications, e.g., with different affinity and/or recognition tags, but all can receive the gene from the master clone. Site-specific recombination sites are located within the expression vector at a location appropriate to receive the coding nucleic acid sequence harbored in the master clone. Particular attention is given to insure that the reading frame is maintained for translation fusions, e.g., to an affinity or recognition tag. To shuttle the gene into the target vector, the master clone vector containing a nucleic acid sequence of interest and the target vector are mixed with the recombinase.

The mixture is transformed into an appropriate bacterial host strain. The master clone vector and the target vector can contain different antibiotic selection markers. Moreover, the target vector can contain a gene that is toxic to bacteria that is located between the recombination sites such that excision of the toxic gene is required during recombination. Thus, the cloning products that are viable in bacteria under the appropriate selection are almost exclusively the desired construct. In practice, the efficiency of cloning the desired product approaches 100%.

To construct the repository, a computer system can be used to automatically design primers based on sequence information, e.g., in a database. Each gene is amplified from an appropriate cDNA library using PCR. The recombination sequences are incorporated into the PCR primers so the amplification product can be directly recombined into a master vector. As described above, because the master vector carries a toxic gene that is lost only after successful recombination, the desired master clone is the only viable product of the process. Once in the master vector, the gene can be verified, e.g., by sequencing methods, and then shuttled into any of the many available expression vectors.

In a preferred embodiment, each gene is cloned twice, i.e., into two master vectors. In one clone, the stop codon is removed to provide for carboxy-terminal fusions. In the other clone, the native stop codon is maintained. This is particularly important for polypeptides whose function is dependent on the integrity of their carboxy-terminus.

Genes in the repository are thus suitable prepared for analysis in activity screens and functional genomics experiments using the NAPPA array. Because of the ease of shuttling multiple genes to any expression vector en masse, these clones can be prepared in multiple array formats, such as those described herein, for a variety of functional assays.

Liu et al. (1998) *Curr. Biol.* 8:1300 describe a Cre-lox based site-specific recombination system for the directional cloning of PCR products. This system uses Cre-Lox recombination and a single recombination site. Here again the master clone is mixed with a target vector and recombinases. However, instead of swapping fragments, the recombination product is a double plasmid connected at the recombination site. This then juxtaposes one end of the gene (whichever end was near the recombination site) with the desired signals in the expression plasmid.

The clone can include a vector sequence and a full-length coding region of interest. The coding region can be flanked by marker sequences for site-specific recombinational cloning, e.g., Cre-Lox sites, or lambda int sites (see, e.g., Uetz et al. (2000) *Nature* 403:623–7). Also, the coding region can be flanked by marker sequences for homologous recombination (see, e.g., Martzen et al. (1999) *Science* 286:1153–5). For homologous recombination almost any sequence can be used that is present in the vector and appended to the coding region. For example, the sequence can encode an epitope or protease cleavage site. After recombination, the full-length coding region can be efficiently shuttled into a recipient plasmid of choice. For example the recipient plasmid can have nucleic acid sequences encoding any one or more of the following optional features: an affinity tag, a protease site, and an enzyme or reporter polypeptide. The recipient plasmid can also have a promoter for RNA polymerase, e.g., the T7 RNA polymerase promoter and/or regulatory sites; a transcriptional terminator; a translational enhancer e.g., a Shine-Dalgamo site, or a Kozak consensus sequence.

Pool Method

A large number of proteins can be screened in one or more passes by the following pooling method. The method uses a first array wherein each address includes a pool of encoding nucleic acid sequences. Addresses identified in a screen with the first array are optionally further analyzed by splitting the pool into different addresses in at least a second array.

Each address of the first array includes a plurality of nucleic acid sequences, each encoding a unique test amino acid sequence and an affinity tag. Thus, each address encodes a pool of test polypeptides. The pools can be random collections, e.g., fractions of cDNA library, or specific collections of sequence, e.g., each address can contain a family of related or homologous sequences, a set of sequence expressed under similar conditions, or a set of sequences from a particular species (e.g., of pathogens). Preferably, a test polypeptide is encoded at only one address of the array.

An interaction detected at a given address by the presence of the second amino acid sequence at an addresses can be further analyzed (e.g., deconvolved) by providing a second array, similar to the first, however, each address containing a nucleic acid sequence encoding a single test polypeptide, the test polypeptide being one of the plurality of test polypeptides at the given address of the first array.

However, arrays with specific collections may not require using a second array. For example, in diagnostic applications, it may suffice to merely identify a collection of sequences.

In another embodiment, an array is used to deconvolve a pool of library sequence identified in a screen that did not rely on arrays to screen initial pools. For example, Kirschner and colleagues describe an in vitro screening method to identify protein interaction partners using radioactively labeled protein pools derived from small pool cDNA libraries (Lustig et al. (1997) *Methods Enzymol.* 283:83–99.). Individual members of such pools can be identified using an array in which unique nucleic acid components of the pool are disposed at unique addresses on the NAPPA platform. An array of sufficient density obviates the need to iteratively subdivide the pool.

In yet another embodiment, the substrate includes a plurality of nucleic acids at each address. The plurality of nucleic acid sequence encodes a different plurality of test polypeptides from the plurality at another address. Each plurality is such that it encodes the components of a protein complex, e.g., a heterodimer, or larger multimer. Exemplary protein complexes include multi-component enzymes, cytoskeletal components, transcription complexes, and signalling complexes. The array can have a different protein complex present at each address, or variation in protein complex composition at each address (e.g., for complexes with optional components, the presence or absence of such components can be varied among the addresses). One or more members of the plurality of test polypeptides can have an affinity tag, preferably just one member has an affinity tag.

In still another embodiment, the plurality of encoding nucleic acids at each address are selected by a computer program which identifies groups of encoding nucleic acids for each address such that if an address is identified, the relevant polypeptide sequence can be determined with little or no ambiguity. For example, for MALDI-TOF detection methods, encoding nucleic acid are grouped such that masses of peptide fragments (e.g., from protease digestions) of the polypeptides encoded by the plurality are distinct, or non-overlapping. Thus, detection of a peptide mass from time-of-flight data at an address would unambiguously identify the relevant polypeptide.

Unnatural Amino Acids

PCT WO90/05785 describes the use of in vitro translation extracts to include unnatural amino acids at defined positions within a polypeptide. In this method, a stop codon, e.g., an amber codon, is inserted in the nucleic acid sequence encoding the polypeptide at the desired position. An amber-suppressing tRNA with an unnatural amino acid is prepared artificially and included in the translation extract. This method allows for alteration at any given position of a polypeptide sequence to an artificial amino acids, e.g., an amino acids with chemical properties not available from the standard amino acid set.

In a preferred embodiment, the amber-suppressing tRNA has an unnatural amino acid with a keto group. Keto groups are particularly useful chemical handles as they are stable in an unprotected form in cell extracts, and able to react with hydrazide and alkoxyamines to form hydrazones and oximes (Cornish et al. (1996) *JACS* 118:8150). Thus, the amber codon can be used as an affinity tag to attach translated proteins to a hydrazide attached to the substrate.

General Applications

The polypeptide arrays described herein can be used in a number of applications. Non-limiting examples are described as follows. The regulation of cellular processes, including control of gene expression, can be investigated by examining protein-protein, protein-peptide, and protein-nucleic acid interactions; antibodies can be screened against an array of potential antigens for profiling antibody specificity or to search for common epitopes; proteins can be assayed for discrete biochemical activities; and the disruption of protein-ligand interactions by synthetic molecules or the direct detection of protein-synthetic molecule interactions can aid drug discovery. Given the versatility of programming the array, elements at each address are easily customized as appropriate for the desired application.

Protein Activity Detection

A nucleic acid programmable array can be used to detect a specific protein activity. Each address of the array is contacted with the reagents necessary for an activity assay. Then an address having the activity is detected to thereby identify a protein having a desired activity. An activity can be detected by assaying for a product produced by a protein activity or by assaying for a substrate consumed by a protein activity.

Protein Interaction Detection

A nucleic acid programmable array can be used to detect protein-protein interactions. Moreover, the array can be used to generate a complete matrix of protein-protein interactions such as for a protein-interaction map (see, e.g., Walhout et al., *Science* 287:116–122, 2000; Uetz et al., *Nature* 403, 623–631, 2000); and Schwikowski (2000) *Nature Biotech.* 18:1257). The matrix can be generate for the complete complement of a genome, proteins known or suspected to be co-regulated, proteins known or suspected to be in a regulatory network, and so forth.

The detection of protein-protein interactions, e.g., between a first and a second protein, entails providing at an address a nucleic acid encoding the first polypeptide and an affinity tag, and a nucleic acid encoding a second polypeptide and a recognition tag, e.g., a recognition tag described below.

In one embodiment, after translation of both nucleic acids, the array is washed to remove unbound proteins and the translation effector. Detection of an address at which the second polypeptide remains bound is indicative of a protein-protein interaction between the first and second polypeptide of that address.

In another embodiment, a third or competing polypeptide can be present during the binding step, e.g., a third encoding nucleic acid sequence lacking a tag can be included at the address.

In yet another embodiment, the stringency or conditions of the binding or washing steps are varied as appropriate to identify interactions at any range of affinity and/or specificity.

Recognition Tags

A variety of recognition tags can be used. For example, an epitope to which an antibody is available can be used as a recognition tag. The tag can be place N or C-terminal to the sequence of interest. The tag is recognized, e.g., directly, or indirectly (e.g., by binding of an antibody).

Green Fluorescent Protein.

Figure 2:
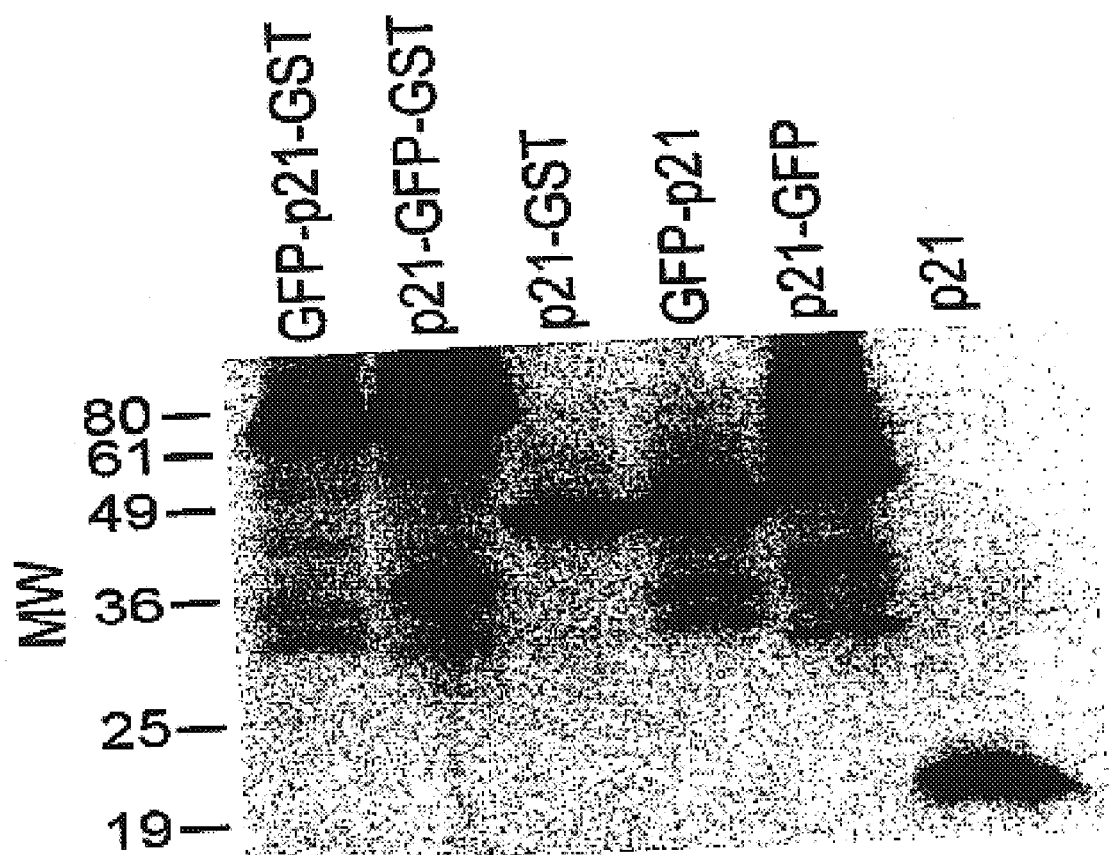
FIG. 2 is a Western blot of an SDS-page gel of in vitro translated GST and GFP fusion proteins. GST- and GFP-p21 fusion proteins were transcribed and translated in a cell-free reticulocyte lysate. Proteins were separated by SDS-PAGE and analyzed by Western blotting with antibodies specific for p21. Sizes of molecular weight markers are shown on the left.

Coding regions of interest are taken from the FLEX repository and transferred into fusion vectors encoding either an N- or C-terminal green fluorescent protein (GFP) tag. These vectors have been made (FIG. 2), and the backbones are similar to those encoding the poly-histidine and GST tags. The GFP-tagged proteins, the query, are co-transcribed/translated with the immobilized target proteins. Target-query complexes are allowed to form, and unbound protein is washed away. Target-query complexes are then detected by fluorescence spectroscopy (Spectra Max Gemini, Molecular Devices). The environment of a fluorophore has a strong effect on the quantum yield of fluorescence (i.e., the ratio of emitted to absorbed photons) through collisional processes and resonance energy transfer (a radiative process), so the concentration of target-query complexes that gives an acceptable signal-to-noise ratio will have to be determined experimentally.

Fluorescence polarization can be used to detect the recognition tag while circumventing the need for immobilization and wash steps to detect protein complexes. When GFP-tagged query is bound to target, the polarization of the fluorescence of GFP increases due to the reduced mobility of the complex, and this increase in polarization can be measured. Conventional fluorescence spectroscopy and fluorescence polarization methods can be used to detect protein-protein interactions. See, e.g., Garcia-Parajo et al. (2000) Proc. Natl. Acad. Sci. USA 97, 7237–7242.

Enzymatic Reporters.

Horseradish peroxidase (HRP) or alkaline phosphatase (AP) polypeptide sequences can be used as the recognition tag. The addition of chromogenic substrate and subsequent calorimetric readout allows for the ready detection of the retention of the second polypeptide. Luciferase can be used as a recognition tag as described in U.S. Pat. No. 5,641,641.

ELISA.

In another embodiment, the second polypeptide lacks a recognition tag. Instead, an antibody is available that recognizes a small common epitope, e.g., common to all second polypeptides located on the array. Target-query complexes are detected with antibodies using enzyme-linked immunosorbent assay (ELISA) techniques as is routine in the art. This embodiment can be preferable if the second polypeptide species is constant among all the addresses, but the first polypeptide species varies.

MS (Mass Spectroscopy).

In yet another embodiment, the recognition tag is a polypeptide sequence whose mass or tryptic profile, when detected by mass spectroscopy, e.g., MALDI-TOF, is indicative of the presence of the second polypeptide. The recognition tag can be a sequence endogenous to the second polypeptide, or an exogenous sequence. Preferably, the MS recognition tag is selected, e.g., using a computer system, to avoid any ambiguity with other potential polypeptide species or tryptic fragments which could be present at each address.

Multipole Coupling Spectroscopy (MCS).

MCS can be used to detect interactions at different addresses of the array. MCS is described, e.g., in PCT WO 99/39190. For example, test polypeptides can be synthesized at different addresses of a molecular binding layer (MBL). The MBL can be coupled at each address of the plurality to interface transmission lines or waveguides. A test signal can be propagate to the MBL and a response detected based on the dielectric properties of the MBL as an indication of binding of a query polypeptide to a test polypeptide at an address. Further, a modulation of the test signal or a dielectric relaxation of the MBL can be detected as an indication of binding of a query polypeptide to a test polypeptide at an address.

Exemplary Protein Complexes

The following exemplary protein complexes can be used to verify or optimize methods or to provide convenient positive and negative controls, e.g., using known interactors of various affinities. Such interactors can include: the signaling proteins cdk4–p16, cdk2–p21, E2F4-p130, and the transcription factors Fos-Jun; components of the DRIP complex (vitamin D Receptor Interacting Proteins; Rachez (1999) *Nature* 398:824 and Rachez (2000) *Mol Cell Biol.* 20:2718).

Protein-DNA Screens

Transcription factors that bind to specific DNA sequences may be identified. Here DNA is the query molecule and can be fluorescently labeled. Alternatively, the DNA can be biotinylated and detected by HRP coupled to avidin.

Protein-Small Molecule Screens

An array described herein can be used to identify a polypeptide that binds a small molecule. The small molecule can be labeled, e.g., with a fluorescent probe, and contacted to a plurality of addresses on the array (e.g., prior, during, or after translation of the programming nucleic acids). The array can be washed after maintaining the array such that the small molecule can bind to a polypeptide with an affinity tag. The signal at each address of the array can be detected to identify one or more addresses having a polypeptide that binds the small molecule.

Other signal detection methods include surface plasmon resonance (SPR) and fluorescence polarization (FP). Methods for using FP are described, for example, in U.S. Pat. No. 5,800,989. Methods for using SPR are described, for example, in U.S. Pat. No. 5,641,640; and Raether (1988) *Surface Plasmons* Springer Verlag.

In another embodiment, the invention features a method of identifying a small molecule that disrupts a protein-protein interaction. The array is programmed with a first and a second nucleic acid which respectively encode a first and second polypeptide which interact. The first polypeptide includes an affinity tag and second polypeptide includes a recognition tag. A unique small molecule is contacted to an address of the array (e.g., prior, during, or after translation of the programming nucleic acids). The array can be washed after maintaining the array such that the small molecule, the first and the second polypeptide can interact. The signal at each address of the array is detected to identify one or more addresses having a small molecule that disrupts the protein-protein interaction.

Pre-Clinical Evaluation of Lead Compounds

An application that exploits the ability to screen for small molecule interactions with proteins could be the pre-clinical evaluation of a lead drug candidate. Drug toxicities often result not from the intended activity on the target protein, but some activity on an unrelated binding protein(s). Even when these adventitious binding proteins do not cause toxicity, they can adversely affect the drug's pharmacokinetics. A comprehensive protein array would make the pre-clinical identification of these adventitious binders rapid and straightforward.

Medicinal Chemistry

The small molecule screen could become a rapid and powerful platform by which medicinal chemistry and SAR could be performed. Chemical modifications of small molecules could be tested against the array to see if changes improve specificity. Compounds could be exposed first to hepatic lysates or other metabolic extracts that mimic metabolism in order to create potentially toxic metabolites that can also be screened for secondary targets. Recursion of this process could lead to improved specificity and tighter binding molecules.

Mass Spectroscopy

The polypeptide array can be used in conjunction with mass spectroscopy, e.g., to detect a modified region of the protein. An array is prepared as described herein with due consideration for the flatness, conductivity, registration and alignment, and spot density appropriate for mass spectroscopy.

In one embodiment, the method identifies a polypeptide substrate for a modifying enzyme. Each address is provided with a nucleic acid encoding a unique test polypeptide. Each address of the array is contacted with the modifying enzyme, e.g., a kinase, a methylase, a protease and so forth. The enzyme can be synthesized at the address, e.g., by include a nucleic acid encoding it at the address with the nucleic acid encoding the test sequence. After sufficient incubation to assay the modification step, each address is proteolyzed, e.g., trypsinized. The resulting peptide mixtures can be subject to MALDI-TOF mass spectroscopy analysis. The combination of peptide fragments observed at each address can be compared with the fragments expected for an unmodified protein based on the sequence of nucleic acid deposited at the same address. The use of computer programs (e.g., PAWS) to predict trypsin fragments is routine in the art. Thus, each address of the array can be analyzed by MALDI. Addresses containing modified peptide fragment relative to a predicted pattern or relative to a control array can be identified as containing potential substrates of the modifying enzyme.

The amount of modifying enzyme contacted to an address can be varied, e.g., from array to array, or from address to address.

For example, this approach can be used to identify phosphorylation by comparing the masses of peptide fragments from an address that having a kinase, and an address lacking the kinase. Pandey and Mann (2000) *Nature* 405:837 describe methods of using mass spectroscopy to identify protein modification sites.

In another embodiment, the modifying enzyme is varied at each address, and the test polypeptide, the polypeptide with the affinity tag for attachment to the substrate, is the same at each address. Both the modifying enzyme and the test polypeptide can be synthesized on the array by translation of encoding nucleic acid sequences. Mass spectroscopy is used to identify an address having a modifying enzyme with specificity for the test polypeptide as enzyme-substrate.

Mass spectroscopy can also be used to detect the binding of a second polypeptide to the target protein. A first nucleic acid encoding a unique target amino acid sequences and an affinity tag is disposed at each address in the array. A pool of nucleic acids encoding candidate amino acid sequence is also disposed at each address of the array. Each address of the array is translated and washed to remove unbound proteins. The proteins that remain bound at each address, presumably by direct interaction with the target proteins, can then be detected and identified by mass spectroscopy.

Assay to Identify Folded Proteins

The NAPPA array can be used to identify appropriately folded protein species, or proteins with appropriate stability. For example, arrays can be provided with a nucleic acid sequence encoding a random amino acid sequence, a designed amino acid sequence, or a mutant amino acid sequence at each address. Such an array can be used to analyze the results of a computer-designed polypeptide, the results of a DNA-shuffling, or combinatorial mutagenesis experiment. The array is contacted with transcription and translation effectors, and subsequently washed provide purified polypeptides at each address.

Subsequently, each address of the array is monitored for a property of the folded species. The property can be particular to the desired polypeptide species. For example, the property can be the ability to bind a substrate. Alternatively, the property can be more general, such as the fluorescence emission profile of the polypeptide when excited at 280 nm. Fluorescence, particularly of tryptophan residues is an indicator of the extent of burial of aromatic groups. Upon denaturation, the center of mass of the fluorescence of exposed tryptophans is shifted. In additional, at an appropriate detection wavelength, the intensity of fluorescence varies with the extent of folding. The array, or selected addresses of the array, can be incrementally exposed to increasing denaturing conditions, e.g., by thermal or chemical denaturation. Thermal denaturation is useful as it does not require altering solutions contacting the array. Thus, if the array contains partitions, subsequent to the washing step, binding of the affinity tag to its handle on the substrate is not required. Addresses showing cooperative folding transitions or increased stability are thus readily identified.

Additional properties for monitoring folding include fluorescent detection of ANS binding, and circular dichroism, Selection Using Display Technologies In another aspect, the NAPPA platform is used to screen—in a massively parallel format—a first collection of polypeptides for binding to members of a second collection of polypeptides.

The first collection of polypeptides is prepared in a display format, e.g., on a bacteriophage, a cell, or as an nucleic acid-polypeptide fusion (Smith and Petrenko (1997) *Chem. Rev.* 97:391; Smith (1985) *Science* 228:1315; Roberts and Szostak (1997) *Proc. Natl. Acad. Sci. USA* 94:12297). For a review of display technologies see Li (2000) *Nat. Biotech.* 18:1251. The first collection can be obtained from any source, e.g., a source described herein. In one illustrative example, the first collection is an artificial antibody library.

The second collection of polypeptides is distributed on an array described herein For example, a nucleic acid encoding each polypeptide of the second collection can be disposed at a unique address of the array. The array is prepared as described herein.

Before, during, or after translation of the encoding nucleic acids, the first collection in display format, termed display polypeptides, is applied to the array. After translation of the encoding nucleic acid, the array is washed to remove unbound display polypeptides. Then, presence of a display polypeptide at at least one address is detected, e.g., by amplification of the nucleic acid portion of nucleic acid-polypeptide fusion; by propagation of a cell or bacteriophage displaying the display polypeptide; and so forth.

Extracellular Proteins

In one embodiment, an extracellular polypeptide or extracellular domain can be displayed on a NAPPA array, e.g., by contacting the array with conditions similar to the extracellular, endoplasmic reticulum, or Golgi milieu. For example, the conditions can be oxidizing or can have a redox potential that is optimized for extracellular protein production. The array can be additionally contacted with modifying enzymes found in the secretory pathway, e.g., glycosylases, proteases, and the like.

In another embodiment, the translation effector is applied in conjuction with vesicles, e.g., endoplasmic reticular structures. The vesicles can include an affinity tag to anchor the vesicle to the array. In such an embodiment, the encoding nucleic acid need not contain an affinity tag.

An array of extracellular proteins or extracellular protein domains can be used to identify interactions with other extracellular proteins; or alteration of living cells (e.g., the adhesive properties, motility, or the secretory repertoire of a cell contacting the the extracellular protein).

Transmembrane Proteins

Transmembrane proteins can be displayed on a NAPPA array by separately producing the nucleic acids encoding the ecto- or extracellular domains, and the cytoplasmic domains. The extracellular domains and the cytoplasmic domains can be encoded at separate addresses or the same address. Alternatively, only one of the two types of domains is encoded on the array.

In another embodiment, the transmembrane domain can be excised. Ottemann et al.(1997) *Proc. Natl. Acad. Sci. USA* 94:11201–4 describe a method for excising a transmembrane domain to generate a soluble functional protein.

In yet another embodiment, in vitro translation on the array further includes providing vesicles derived from endoplasmic reticulum.

Contacting Array with Cells

In another embodiment, at least one address of the array, e.g., after translation of encoding amino acids, is contacted with a living cell. After contacting the array, the cell or a cell parameter is monitored. For example, polypeptide growth factors can be arrayed at different addresses, and cells assayed after contact to each address. The cells can be assayed for a change in cell division, apoptosis, gene expression (e.g., by gene expression profiling), morphology changes, differentiation, proteomics analysis (e.g., by 2-D gel electrophoresis and mass spectroscopy), and specific enzymatic activities.

In one embodiment, a test polypeptide of the array can be detached from the substrate of the array, e.g., by proteolytic cleavage at a specific protease site located between the test sequence and the tag.

In another embodiment, the test polypeptide does not have an affinity tag, but is maintained at an address by physical separation from other addresses of the plurality. The translation effector is optionally not washed from the address. Cells are assayed after being maintained at the address as described above.

Cell-Free Assay Platforms

High-throughput, genome-wide screens for protein-protein, protein-nucleic acid, protein-lipid, protein-carbohydrate, and protein-small molecule interactions can be performed on an array described herein. Each address of the array can include a polypeptide encoded by a nucleic acid clone from a repository of full-length genes, e.g., genes stored in a vector that facilitates rapid shuttling by recombinational cloning.

Kits

Kits are convenient collections of components, e.g., reagents that can be supplied to a user in order to efficiently enable the user to practice a method described herein.

Universal Primer Kit.

A universal primer kit provides a simple means for amplifying a collection of encoding nucleic acid sequences in a format suitable for disposal on an array. The kit includes a 5' universal primer and a 3' universal primer. The kit can further include a substrate, e.g., with an appropriate binding agent attached thereto.

The 5' primer can include the T7 promoter and a 5' annealing sequence, whereas the 3' primer can include a 3' annealing sequence and sequence encoding an affinity tag. Nucleic acid coding sequences amplified with the 5' annealing sequence and the 3' annealing sequence are further amplified with the universal primer set. The products of this amplification are amenable for immediate disposal on the array.

Moreover, asymmetric PCR can be utilized to create an excess of the coding strand. Single-stranded DNA can be deposited on the array and annealed to a T7 promoter nucleic acid capture probe in order to provide a duplex recruitment site for T7 polymerase.

The kit can further include transcription and/or translation effectors, reagents for amplification, and buffers.

Recombinational Cloning Kit.

A recombinational cloning kit provides tools for shuttling multiple encoding nucleic acid sequences, preferably en masse, into a vector having suitable regulatory sequences, and affinity tag-encoding sequence for the NAPPA platform. The kit includes a substrate with multiple addresses, each addressing having a binding agent attached to the substrate. The kit also includes a vector having sequences for generating encoding nucleic acid with affinity tags. Once a nucleic acid sequence is cloned into the vector, the nucleic acid of the vector with the insert is suitable for programming the array.

The vector can include a recombination site, e.g., a site-specific recombination site, or a homologous recombination site. Alternatively, the vector can include unique restriction sites, e.g., for 8-bp cutters, in order to facilitate subcloning sequence encoding test polypeptides. These features facilitate the rapid, and parallel construction of multiple coding nucleic acids for programming the array. Thus, a complex array having many unique polypeptide sequences can be easily produced.

For example, a repository of cloned full-length coding sequences of interested flanked by recombination sites is constructed. Multiple sequences in the repository are shuttled into the vector using in vitro site-specific recombination and enhanced selection techniques (see description of Recombinational cloning above, and The Gateways Manual, Invitrogen, CA). Robotics and microtiter plates can be used to rapidly producing the multiple coding nucleic acids for programming the array.

The kit can further include a second vector having recombination sites, appropriate regulatory sequences, and a recognition tag, such as a recognition tag described herein. The user can thus shuttle a nucleic acid encoding a sequence of interest into both a vector with an affinity tag, and a vector with a recognition tag. This compatibility facilitates the generation of protein-protein interaction matrices.

A Network Architecture for Providing a NAPPA Array

Figure 3:
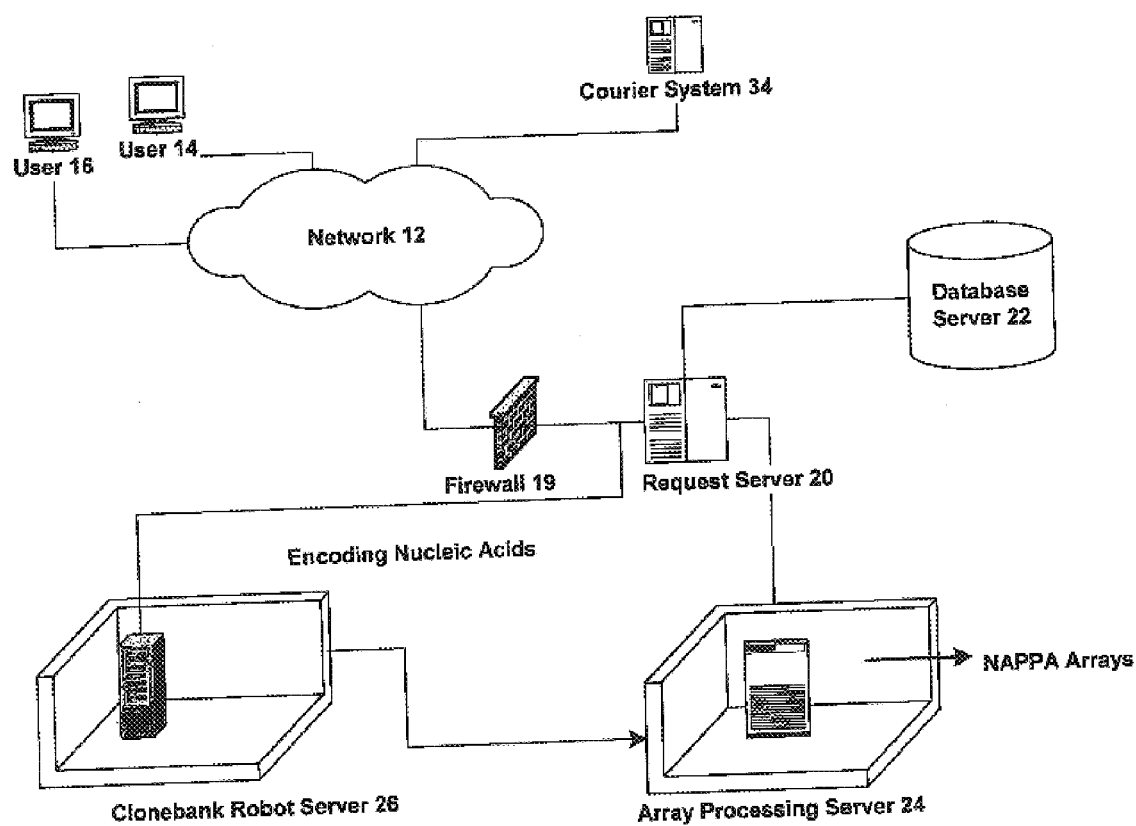
FIG. 3 is a schematic of a computer network for providing NAPPA microarrays.

Referring to FIG. 3, a user system 14 and a request server 20 are connected by a network 12, e.g., an intranet or an internet. For example, the user system and the request server can be located within a company, the user system in a research department, and the request server in an applications department. Alternatively, the user system 14 can be located within one company, e.g., in a diagnostics division, and the request server 20 can be located in a second company, e.g., a protein microarray provider. The companies can be connected by a network, e.g., by the Internet, a proprietary network, a dial-up connection, a wireless connection, an intermediary, or a customized procurement network. A network within a company can be protected by a firewall 19.

The request server 20 is connected to a database server 22. The database server 22 can contain one or more tables with records to amino acid sequences of polypeptides (e.g., a relational database). For example, each record can contain one or more fields for the following: the amino acid sequence; the location of a nucleic acid clone encoding the nucleic acid in a repository or clone bank; category field; binding ligands of the polypeptide; co-localizing and/or binding polypeptides; links (e.g., hypertext links to other resources); and pricing and quality control information. The database can also contain one or more tables for classes and/or subsets of amino acid sequence. For example, a class can contain entries for amino acid sequences expressed in a particular tissue, correlated with a condition or disease, originating from a species, having homology to a protein family, related to a biological (e.g., physiological or cellular) process, and so forth.

The request server 20 sends to the user 14 one more choices for amino acid sequence to include on a microarray. The choices are provided in a user-friendly format e.g., a hypertext page with forms (e.g., selection boxes). The choices can be hierarchical, e.g., a first list of choices to determine general user needs, and subsequent choices e.g., of a class of amino acid sequence, or of individual amino acid sequences. The choices can also include pre-designed microarrays, as well as individually customized designs. The server can also recommend appropriate negative and positive control amino acid sequence to include depending on previous selections. Alternatively, the system can be voice based, the queries and selections are transmitted across a telecommunications network, e.g., a telephone, a mobile phone, etc.

The user indicates selections, e.g., by clicking on a form provided on a web page. The request server forwards the selections, e.g., the location of nucleic acid encoding a selected amino acid sequence in a clone bank, to a clone bank robot controller. The robot controller 26 mobilizes a robot to access the clone bank and obtain the desired encoding nucleic acid. Optionally, the nucleic acid can be shuttled from a repository vector into an expression vector using recombinational cloning techniques. In another possible implementation, the nucleic acid stored in the repository is already in an appropriate expression vector for nucleic acid programmable protein microarray production. In still another possible implementation, the nucleic acid is amplified with primers which contain the requisite flanking sequence for disposal on the microarray. For example, one or more primers can include a T7 promoter, and/or an affinity tag.

Once obtained, the nucleic acid is provided to an array maker. The array processing server 24 is also interfaced with the request server 20 and the robot controller 26. The nucleic acid is deposited onto one or more array substrates, e.g., using a method described herein. The array production controller selects one or more addresses at which the nucleic acid is deposited, and records the addresses in a table associated with the array being produced. The array production controller can also vary the amount and method of deposition for any particular sample or address. Such variables and additional quality control information is also stored in the table.

For example, if multiple identical arrays are produced in parallel, one or more arrays can be used for a quality control testing. For example, transcription and translation effectors can be contacted to the array at the production facility. The presence of selected or control proteins is verified by contacting the array with specific antibodies for such proteins, and detecting the binding.

Once produced, an array is prepared for shipping, for example, contacted with a preservative solution, dessicated, and/or coated in an emulsion, film, or plastic wrap. The request server 20 interfaces with a courier system 34, e.g., to track shipment and delivery of the array to the user. The request server also notifies the user of the status of the array production and shipment throughout the procurement process, e.g., using electronic mail messages.

The request server interfaces with a business-to-business server to initiate appropriate billing and invoicing as well as to process customer service requests.

Diagnostic Assays

A variety of polypeptide microarrays can be provided for diagnostic purposes. The array can be used as a screening tool to look for antibodies that bind to specific proteins. This could be applied for the generation of monoclonal antibodies in a high-throughput setting or in the context of measuring immune responses in a patient. ELISA techniques can be used for detection.

Antigen Arrays.

One class of such arrays is an array of antigens, displayed for the purpose of determining the specificity of antibodies in a subject. The array is programmed such that each address represents a different antigen of a pathogen or of a malady (e.g., antigens significant in allergies; transplant rejection and compatibility testing; and auto-immune disorders).

In one embodiment, the array has antigens from a plurality of bacterial organisms. Computer programs can be optionally used to predict likely antigens encoded by the genome of an organism (Pizza et al (2000) *Science* 287:1816). In a preferred embodiment, each address has disposed thereon a unique antigen. In another preferred embodiment, each addresses has a plurality of antigens, all being from the same species. Thus, for example, binding of a subject's antibody to an address indicates that the subject has been exposed to a pathogen represented by the address.

In another preferred embodiment, the array is used to track the progression of complex diseases. For example, diseases with antigenic variation (e.g., malaria, and trypanosomiasis) can be accurately diagnosed and/or monitored by identifying the repertoire of specific antibodies in a subject.

In another embodiment, the array can be used to detect the specific target of an autoimmune antibody. For example, isolated antibodies or serum from a subject having type I diabetes are contacted to an array having islet-cell specific proteins present at different addresses of the array.

Antigen arrays also provide a convenient means of monitoring vaccinations and disease exposure, e.g., in epidemiological studies, veterinary quarantine, and public health policy.

Antibody Arrays.

A second class of diagnostic arrays is arrays of antibodies. A variety of methods are available for identifying antibodies. Monoclonal antibodies against a variety of antigens are identified. The nucleic acids encoding such antibodies are sequenced from the genome of hybridoma cells. The nucleic acid sequence is used to engineer single-chain variants of the antibody. Thus, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). The encoding nucleic acid sequence can be recombined into an appropriate vector, e.g., a vector described above with promoter and affinity tag encoding sequences.

In addition, the antibody sequence can be engineered to remove disulfides (Proba K (1998) *J Mol. Biol.* 275:245–53). Alternatively, after translation and washing of the array, the array is subject to oxidizing conditions, e.g., by contacting with glutathione. The antibodies can be coupled to the array with streptococcal protein G, or *S. aureus* protein A. Further, specialized antibodies such as modified or CDR-grafted version of naturally occurring antibodies devoid of light chains can be used. The antibodies of camel (e.g., Camelus dromedaries) are naturally devoid of light chains (Hamers-Casterman C (1993) *Nature* 363:446–8; Desmyter et al. *Nat Struct Biol* September 1996;3(9): 803–11).

A patient sample can then be contacted to the array. Non-limiting examples of patient samples include serum proteins, proteins extracted from a biopsy obtained from the patient, and so forth. In addition, cells themselves can be contacted to the array in order to query for antigens displayed on the cell surface.

In one embodiment, the sample is modified with a compound prior to being contacted to the array. For example, the sample can be biotinylated. Addresses that bind proteins in the sample are then identified by contacting the array with labeled streptavidin or labeled avidin. In another embodiment, the sample is unlabelled. MALDI, SPR, or another techniques are used to identify if a protein is bound at each address. Arrays can be designed to identify proteins associated with various maladies, e.g., to detect antigens associated with cancer at various stages (for example, early, and pre-metastatic stages) or to provide a prediction (for example, to quantitate the abundance of an antigen correlated with a condition).

Vaccine Development

The NAPPA arrays provide an improved method for developing a vaccine. One preferred embodiment includes identifying possible antigens for use in a vaccine from the sequenced genome of a pathogen. Pizza et al. (2000) *Science* 287:1816 describe routine computer-based methods for identifying ORFs which are potentially surface exposed or exported from a pathogenic bacteria. The method further includes making 1) a nucleic acid that serves as a DNA vaccine for expressing each candidate antigen, and 2) a nucleic acid encoding the ORF and an affinity tag in order to program an array. The recombination cloning methods described herein are amenable for generating such a collection of nucleic acids.

The nucleic acids serving as a DNA vaccine can be assembled into multiple random pools and used to immunize a plurality of subjects, e.g., mice. Subsequently, each immunized subject is challenged with the pathogenic organism. Serum is collected from subjects with improved immunity.

An array is provided with a unique encoding nucleic acid at each address. The array is translated and then contacted with the serum from a subject with improved immunity. Binding of a serum antibody to an address are indicative of the address having a polypeptide that is an antigen useful for vaccination against the pathogen.

In another embodiment, a DNA vaccine is substituted with conventional injection of antigens, e.g., as described in Pizza et al., supra.

Network for Diagnostic Assay

Figure 4:
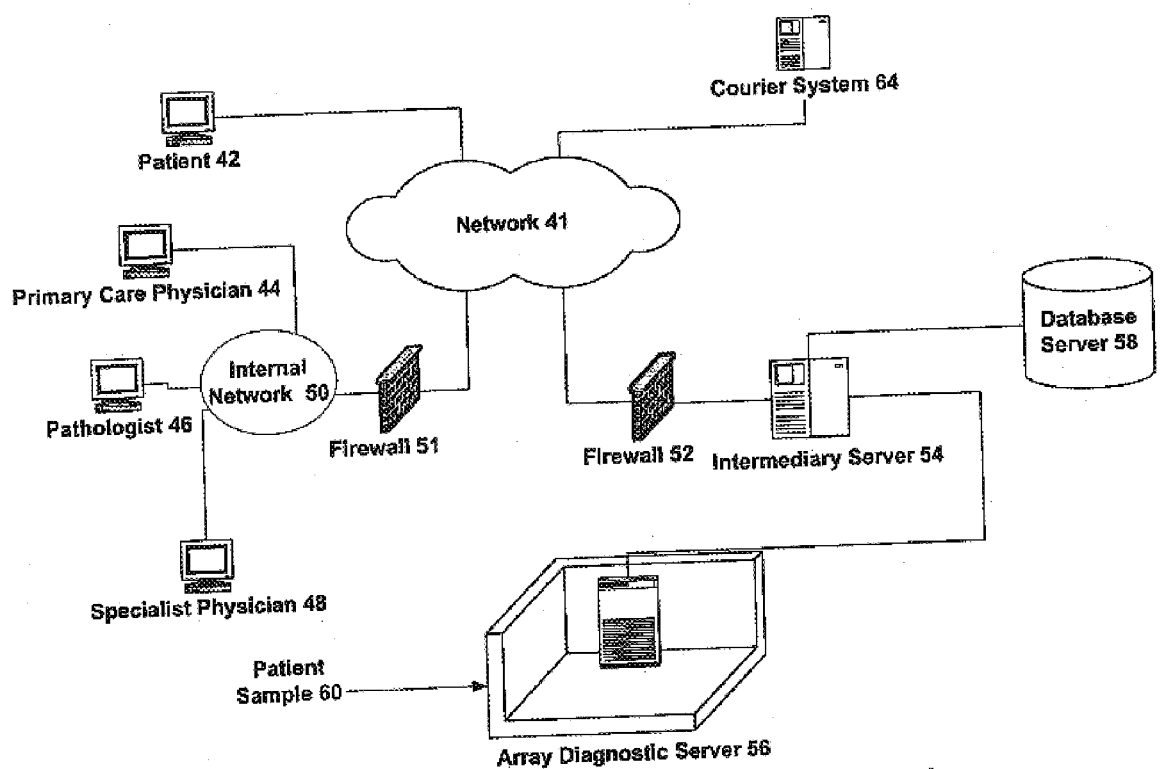
FIG. 4 is a schematic of a computer network for providing diagnostic services.
Figure 5:
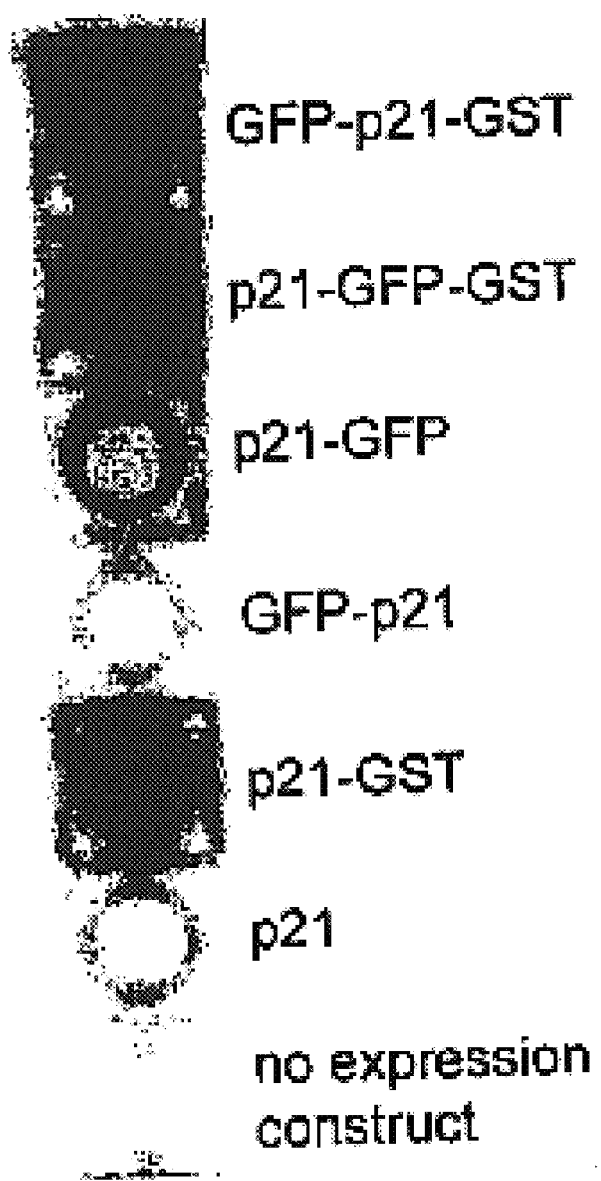
FIG. 5 is a picture of a NAPPA array. GST is used as an affinity tag and is fused to test amino acid sequences such as p21. Cell-free (reticulocyte lysate) transcription/translation and detection of fusion proteins in wells coated with antibodies specific for GST. Coupled transcription/translation for 1.5 hrs at 30° C. was followed by swirling for 1.5 hrs at 22° C. to allow GST-fusion proteins to bind to the wells. A wash with PBS was followed by the detection of immobilized proteins with a p21-specific primary antibody and a mouse-specific HRP-conjugated secondary antibody. The wells containing expressed GST-fusion proteins provide the dominant signal, indicating specific immobilization of target proteins. Applications for using an array of antigens for determining the specificity of antibodies in a subject are described, e.g., in the "Diagnostic Assays" section of the text.
Figure 6:
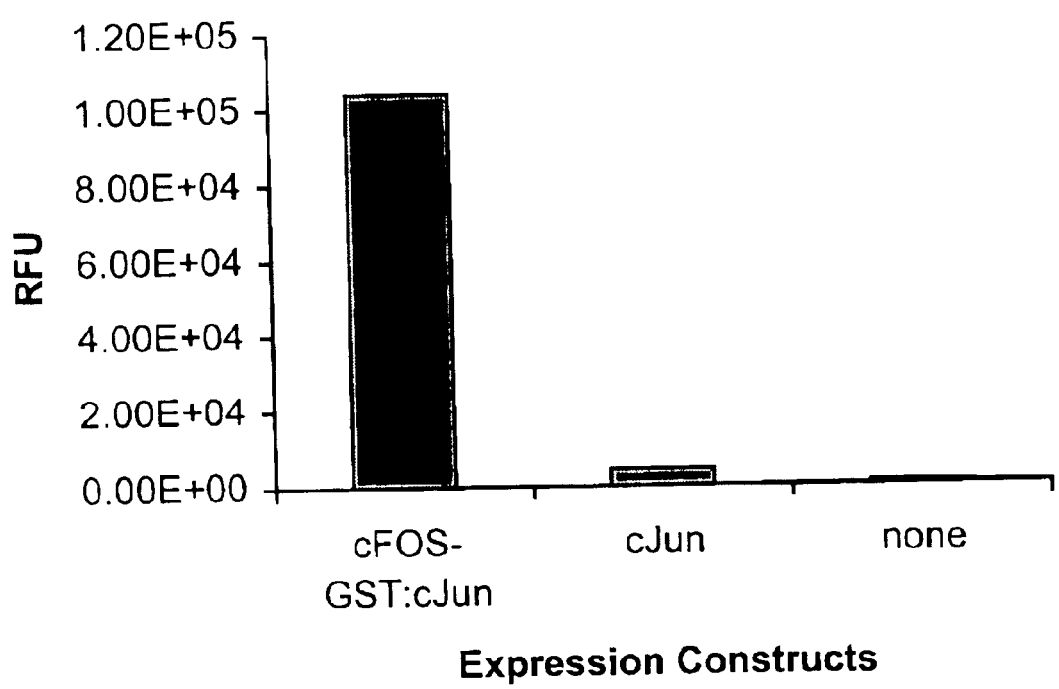
FIG. 6 is a graph of binding of c-jun to c-fos detected on a NAPPA array. Cell-free (reticulocyte lysate) transcription/translation of the interacting transcription factors cFos-GST and cjun, cJun only, and a no plasmid control in wells coated with antibodies specific for GST. Coupled transcription/translation for 1.5 hrs at 30° C. was followed by swirling for 1.5 hrs at 22° C. to allow cFos-GST to bind to the well and cJun to bind to cFos-GST. A wash with PBS was followed by the detection of a cFos:cJun complex with a cJun-specific primary antibody and a mouse-specific HRP-conjugated secondary antibody. Chemiluminescence was measured in RLU (Relative Luminescence Units) by luminometry. Immobilized cFos-cJun complex resulting from cell-free coexpression was clearly detected above background signal.

Referring to FIG. 4, a network links health care providers 50, subjects 42, and an intermediary server for the purpose of providing results of diagnostic NAPPA arrays. Health care providers can include a primary care physician 44; and a specialist physician 48, e.g., infectious disease specialist, rheumatologist, hematologist, oncologist, and so forth; and pathologists 46. Within a health care institution, such providers can be linked by an internal network 50 attached to an external network 41 by a firewall 51. Alternatively, the providers can be located on different internal networks that can communicate, e.g., using secure and/or proprietary protocols. The external network can be the Internet or other well-distributed telecommunications network.

The subject can be a human patient, an animal, a forensics sample, or an environmental sample (e.g., from a waste system).

A sample, e.g., of blood, cells, biopsy, serum, or bodily fluid, provided by the subject is delivered to the array diagnostic service, for example by a courier. Tracking provided by the courier system 64 can monitor delivery. The delivered sample is analyzed according to instructions, e.g., accompanying the sample, or provided across the network. The instructions can indicate suspected disorders and/or requested assays.

The array is programmed such that after translation, each address will contain a different antigen or antibody (e.g., as described above). For common diagnostics, NAPPA arrays can be prepared in bulk at the same or another facility.

The sample is optionally processed and then is contacted to a nucleic acid programmable array, e.g., before or after translation to the encoding nucleic acid. Sample handling and detection can be controlled automatically by the array diagnostic server 56 which is interfaced with robotic and detection equipment. The binding of the sample to the array is then detected by the array diagnostic server 56. Addresses wherein binding of the sample to the array is detected are recorded, e.g., in a table that is store in a database server 58. An intermediary server 54 is used to transmit results, e.g., securely, back to the health care providers, e.g., the primary care physicians 44, and the specialist 48. Optionally, the patient or subject can be directly notified if results are available.

The results can be stored in the database server 58 and/or transmitted to one or more of the physicians, and health-care providers. The results also may be made available e.g., for meta-analysis by public health authorities and epidemiologists.

Informatics

A computer system, containing a repository of observed interaction is also featured. The computer system can be networked to receive data, e.g., raw data or processed data, from a data acquisition apparatus, e.g., a microchip slide scanner, or a fluorescence microscope.

The computer system includes a relational database. The database houses all data from multiple screens, e.g., using different arrays. One table contains table rows for each experiment, e.g., describing the microarray production number, experiment date, experimental conditions, and so forth. The raw data from a GFP-based interaction microarray experiment, for example, is stored in a second table with table rows for each address on the array. The second table has fields for observed fluorescence, background fluorescence, the amino acid sequences present at the microarray address, other annotations, links, cross-references and so forth.

Thus, the database provides a comprehensive catalog of biomolecular interactions. The system is designed to facilitate digital access to the data in order to interface the experimental results with predictive models of interactions. The system can be accessed in real time, e.g., as microarray data is acquired, and from multiple network stations, e.g., multiple users within a company (e.g., using an Intranet), multiple customers of a data provider (e.g., using secure Internet communication protocols), or multiple individuals across the globe (e.g., using the Internet).

Clustering algorithm can be applied to records in the database to identify addresses which are related. See, e.g., Eisen et al. ((1998) *Proc. Nat. Acad. USA* 95:14863) and Golub et al. ((1999) *Science* 286:531) for methods of clustering microarray data.

Other embodiments are within the following claims.

What is claimed:

1. A method comprising:
   providing a substrate that comprises a plurality of addresses, each address comprising (i) a nucleic acid encoding a hybrid amino acid sequence comprising a test amino acid sequence and an affinity tag, and (ii) a binding agent that recognizes the affinity tag;
   contacting each address of the plurality with a translation effector to thereby translate the hybrid amino acid sequence; and
   maintaining the substrate under conditions permissive for the hybrid amino acid sequence to bind the binding agent.

2. The method of claim 1 further comprising contacting cells to the substrate and evaluating the cells or a parameter of the cells.

3. The method of claim 1 further comprising contacting members of a display library to the substrate.

4. The method of claim 1 further comprising contacting a patient sample to the substrate.

5. The method of claim 4 further comprising further comprising detecting binding of the patient sample to the array.

6. The method of claim 5 further comprising recording results of the detecting in a database.

7. The method of claim 1 wherein the test amino acid sequences at the plurality of addresses comprise allergens and/or auto-immune antigens.

8. The method of claim 1 wherein the test amino acid sequences at the plurality of addresses comprise naturally occurring sequences.

9. The method of claim 8 wherein the test amino acid sequences at the plurality of addresses comprise bacterial antigens.

10. The method of claim 8 wherein the test amino acid sequences at the plurality of addresses comprise viral antigens.

11. The method of claim 10 wherein the viral antigens comprise antigens from a rotavirus, hepatitis virus, herpes virus, papilloma virus and/or a retrovirus.

12. The method of claim 1 wherein the test amino acid sequences at the plurality of addresses comprise artificial amino acid sequences.

13. The method of claim 1 wherein the test amino acid sequences at the plurality of addresses comprise transmembrane proteins whose transmembrane domains have been excised.

14. The method of claim 1 wherein the test amino acid sequences at the plurality of addresses comprise randomized amino acid sequences.

15. The method of claim 1 wherein the test amino acid sequence comprises an immunoglobulin variable domain.

16. A The method of claim 1 further comprising contacting endoplasmic reticulum vesicles to the array.

17. The method of claim 1 wherein each address contains less than 1 ng of the nucleic acid.

18. The method of claim 1 wherein each address contains less than 10 pg of the nucleic acid.

19. The method of claim 1 wherein each address further comprises a nucleic acid encoding a modifying enzyme.

20. The method of claim 1 wherein the modifying enzyme is varied among the addresses of the plurality.

21. The method of claim 1 further comprising evaluating the substrate for a fluorescence.

22. The method of claim 1 further comprising evaluating the substrate using mass spectroscopy.

23. The method of claim 1 further comprising evaluating the substrate for a fluorescent property.

24. The method of claim 1 further comprising evaluating the substrate for an enzymatic property.

25. The method of claim 1 further comprising evaluating the plurality of addresses on the substrate, and recording results of the evaluating in records of a database.

26. The method of claim 25 further comprising clustering the records to identify addresses which are related.

27. The method of claim 25 further comprising making results of the evaluating accessible to a network of health care providers.

28. The method of claim 25 further comprising making results of the evaluating accessible to a physician.

29. The method of claim 1 wherein the providing of the substrate comprises:
providing a collection of nucleic acids, each member of the collection being compatible with a recombinational cloning system and including an open reading frame of interest;
recombining members of the collection with a recipient nucleic and that comprises a nucleic acid sequence encoding an affinity tag such that the open reading frame is linked in frame to the nucleic acid sequence encoding the affinity tag; and
disposing nucleic acid derived from the recombination at addresses of the plurality of addresses.

30. The method of claim 1 further comprising contacting each address of the plurality with a transcription effector.

31. The method of claim 1 further comprising contacting each address of the plurality with a transcription effector and a translation effector.

32. The method of claim 1 wherein the translation effector comprises a translation extract prepared from cells.

33. The method of claim 1 further comprising contacting each address of the plurality with a chaperone.

34. The method of claim 1 wherein each test amino acid sequence is unique.

35. The method of claim 1 wherein the affinity tag is separated from the test amino acid sequence by at least five amino acids.

36. The method of claim 1 wherein the affinity tag encoded by the nucleic acid at each address of the plurality is the same.

37. The method of claim 1 wherein the affinity tag encoded by the nucleic acid at an address of the plurality differs from at least one other affinity tag in the plurality of addresses.

38. The method of claim 1 wherein the nucleic acid is DNA.

39. The method of claim 38 wherein the nucleic acid is double stranded DNA.

40. The method of claim 38 wherein the nucleic acid comprises an operably linked transcription promoter.

41. The method of claim 1 wherein the nucleic acid comprises an internal ribosome entry site.

42. The method of claim 1 wherein the nucleic acid comprises a plurality of cistrons.

43. The method of claim 1 wherein the nucleic acid comprises a sequence that encodes a reporter protein.

44. The method of claim 43 wherein the reporter protein can produce or modulate light.

45. The method of claim 1 wherein the transcription promoter is a prokaryotic promoter.

46. The method of claim 1 wherein the amino acid sequence comprises an intein.

47. The method of claim 1 wherein the substrate is partitioned.

48. The method of claim 1 wherein the substrate comprises at least 1 address per 2 cm.

49. The method of claim 48 wherein the substrate comprises at least 10 addresses per $cm^2$.

50. The method of claim 1 wherein the binding agent comprises a biological polymer.

51. The method of claim 1 wherein the binding agent is covalently attached to the substrate.

52. The method of claim 1 wherein the binding agent is attached by a bridging moiety.

53. The method of claim 1 wherein the binding agent is an antibody.

54. The method of claim 1 wherein the affinity tag comprises a polypeptide sequence which can chelate metal.

55. The method of claim 54 wherein the affinity tag comprises hexa-histidine.

56. The method of claim 1 wherein the affinity tag comprises a protein selected from the group consisting of glutathione-S-transferase, chitin binding protein, cellulase, maltose binding protein, dihydrofolate reductase, and FK506 binding protein (FKBP).

57. The method of claim 1 further comprising contacting each address of the plurality with a protein-modifying enzyme.

58. The method of claim 1 wherein the nucleic acid comprises a site-specific recombination site.

59. The method of claim 1 wherein each address comprises a plurality of nucleic acid sequences, each encoding a unique test amino acid sequence and an affinity tag.

60. The method of claim 1 wherein the providing comprises mechanically delivering the nucleic acid to each address of the plurality of addresses.

61. The method of claim 1 wherein the providing comprises amplifying a template nucleic acid to provide a nucleic acid for each address of the plurality of addresses.

62. The method of claim 1 wherein the substrate is glass.

63. The method of claim 62 wherein the substrate is a glass slide.

64. The method of claim 1 wherein the substrate comprises a planar array.

* * * * *